US007794733B2

(12) United States Patent
Judd et al.

(10) Patent No.: US 7,794,733 B2
(45) Date of Patent: Sep. 14, 2010

(54) OMP85 PROTEINS OF *NEISSERIA GONORRHOEAE* AND *NEISSERIA MENINGITIDIS*, COMPOSITIONS CONTAINING SAME AND METHODS OF USE THEREOF

(75) Inventors: Ralph C. Judd, Florence, MT (US); D. Scott Manning, Missoula, MO (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 10/606,618

(22) Filed: Jun. 26, 2003

(65) Prior Publication Data

US 2005/0074458 A1 Apr. 7, 2005

Related U.S. Application Data

(63) Continuation of application No. 09/994,192, filed on Nov. 26, 2001, now Pat. No. 6,610,306, which is a continuation of application No. 09/177,039, filed on Oct. 22, 1998, now abandoned.

(51) Int. Cl.
*A61K 39/095* (2006.01)
*A61K 39/02* (2006.01)
*A61K 39/00* (2006.01)
*A61K 39/38* (2006.01)
*A61K 38/00* (2006.01)
*C07K 14/00* (2006.01)

(52) U.S. Cl. .............. 424/250.1; 424/234.1; 424/249.1; 424/190.1; 424/184.1; 424/192.1; 514/2; 530/350; 530/825

(58) Field of Classification Search .............. 424/234.1, 424/190.1, 184.1, 192.1, 249.1, 250.1; 530/350, 530/825, 300; 435/975, 7.2; 514/2
See application file for complete search history.

(56) References Cited

U.S. PATENT DOCUMENTS

| 5,554,372 | A | * | 9/1996 | Hunter ..................... 424/280.1 |
| 5,698,438 | A | | 12/1997 | Stojiljkovic .............. 435/252.3 |
| 5,708,155 | A | | 1/1998 | Potter ........................ 536/23.4 |
| 5,834,591 | A | | 11/1998 | Normark .................... 530/350 |
| 5,912,336 | A | | 6/1999 | Sparling .................... 536/23.7 |
| 6,197,301 | B1 | | 3/2001 | Flavell ..................... 424/190.1 |
| 6,348,185 | B1 | * | 2/2002 | Piwnica-Worms ......... 424/1.69 |
| 6,551,795 | B1 | * | 4/2003 | Rubenfield et al. ......... 435/69.1 |
| 6,610,306 | B2 | | 8/2003 | Judd ........................ 424/250.1 |
| 6,709,660 | B1 | | 3/2004 | Scarlato et al. ........... 424/250.1 |
| 2004/0033234 | A1 | * | 2/2004 | Berinstein et al. ......... 424/185.1 |
| 2004/0126391 | A1 | | 7/2004 | Scarlato et al. .......... 424/190.1 |
| 2005/0074458 | A1 | | 4/2005 | Judd et al. |
| 2005/0191316 | A1 | | 9/2005 | Fraser et al. ............. 424/190.1 |
| 2005/0287165 | A1 | | 12/2005 | Scarlato et al. .......... 424/190.1 |

FOREIGN PATENT DOCUMENTS

| EP | 474313 | A2 | 3/1992 |
| EP | 1 535 928 | | 7/2008 |
| WO | WO-92/03467 | A1 | 3/1992 |
| WO | WO 94/12641 | * | 6/1994 |
| WO | WO-98/21333 | A2 | 5/1998 |
| WO | WO 99/24578 | A2 | 5/1999 |
| WO | WO 99/36544 | A2 | 7/1999 |
| WO | WO 99/57280 | A2 | 11/1999 |

OTHER PUBLICATIONS

Skolnick et al. Trends in Biotechnology 18: 34-39, 2000.*
Harlow et al. In: Antibodies: A Laboratory Manual. Cold Spring Harbor Laboratory, Chapter 5, p. 76, 1988.*
Protein Sequences on STN, p. 12.*
Kawarabayashi et al. DNA Res. 5: 55-76, 1998.*
Albertini et al. J. Bacteriol. 173: 3573-3579, 1991.*
Wetzler et al. J. Exp. Med. 169: 2199-2210, 1989.*
Harlow et al. In: Antibodies: a Laboratory Manual. Cold Spring Harbor Laboratory, New York, pp. 471-510, 1988.*
Cruse et al., Illustrated Dictionary of Immunology, 2nd Edn., CRC Press, pp. 46, 166 & 382, 2003.*
Colman PM. Research Immunol. 145: 33-36, 1994.*
McGuinnes et al. Mol. Microbiol. 7: 505-514, Feb. 1993.*
McGuinnes et al. Lancet 337: 514-517, Mar. 1991.*
Dunn et al. Microbial Pathogenesis 18: 81-96, 1995.*
Mignogna et al. J. Proteome Res. 4: 1361-1370, 2005.*
West et al. Infect. Immun. 47: 388-394, 1985.*
Wedege et al. Clin. Vaccine Immunol. 14: 830-838, Jul. 2007.*
Norheim et al. Vaccine 23: 3762-3774, 2005.*
Flack et al., "The Sequencing of the 80-kDA D15 Protective Surface Antigen of *Haemophilus influenzae*", Gene, 156-97-99 (Apr. 4, 1995).
Thomas et al., "Expression in *Escherichia coli* of a High-Molecular-Weight Protective Surface Antigen Found in Nontypeable and Type B *Haemophilus influenzae*", Infection and Immunity, 58(6):1909-1913 (Jun. 1990).
Ruffolo et al., "Cloning, Sequencing, Expression, and Protective Capacity of the oma87 Gene Encoding the *Pasteurella multocida* 87-Kilodalton Outer Membrane Antigen", Infection and Immunity, 64(8):3161-3167 (Aug. 1996).
Loosmore et al., "Outer Membrane Protein D15 is Conserved Among *Haemophilus influenzae* Species and May Represent a Universal Protective Antigen Against Invasive Disease", Infection and Immunity, 65(9):3701-3707 (Sep. 1997).
Elkins et al., "Species-Specific Uptake of DNA by Gonococci is Mediated by a 10-Base-Pair Sequence", J. Bacteriology, 173(12):3911-3913 (Jun. 1991).

(Continued)

*Primary Examiner*—S. Devi
(74) *Attorney, Agent, or Firm*—Howson & Howson LLP

(57) ABSTRACT

Nucleic acid and amino acid sequences of the Omp85 proteins of *N. gonorrhoeae* and *N. meningitidis*, and fragments thereof are useful in vaccine compositions, therapeutic compositions and diagnostic compositions for use in the prevention, treatment and diagnosis of non-symptomatic gonococcal infection or symptomatic disease and non-symptomatic meningococcal infection and symptomatic disease. Antibodies are developed to these proteins and also useful in the compositions and methods described herein.

1 Claim, 10 Drawing Sheets

OTHER PUBLICATIONS

Von Heijne et al., "A New Method for Predicting Signal Sequence Cleavage Sites", Nucleic Acids Research, 14(11):4683-4690 (1986).

Struyve et al., "Carboxy-Terminal Phenylalanine is Essential for the Correct Assembly of a Bacterial Outer Membrane Protein", J. Mol. Biol., 2118:141-148 (Mar. 5, 1991).

Altschul et al., "Basic Local Alignment Search Tool", J. Mol. Biol., 215:403-410 (Oct. 5, 1990).

Tomb et al., "The Complete Genome Sequence of the Gastric Pathogen *Helicobacter pylori*", Nature, 388:539-547 (Aug. 1997).

Fraser et al., "Genomic Sequence of a Lyme Disease Spirochete, *Borrelia burgdorferi*", Nature, 390:580-586 (Dec. 1997).

Koski et al., "Isolation, Cloning, and Primary Structure of a Cationic 16-kDa Outer Membrane Protein of *Salmonella typhimurium*", J. Biol. Chem., 264(32):18973-18980 (Nov. 1989).

Fleischmann et al., "Whole-Genome Random Sequencing and Assembly of *Haemophilus influenzae* Rd", Science, 269:496-512 (Jul. 1995).

Rossau et al., "Ribosomal Ribonucleic Acid Cistron Similarities and Deoxyribonucleic Acid Homologies of *Neisseria, Kingella, Eikenella, Simonsiella, Aysiella*, and Centers for Disease Control Groups EF-4 and M-5 in the Amended Family *Neiseriaceae*", International Journal of Systematic Bacteriology, 39:185-198 (Apr. 1989).

Schnell et al., "Isolation of Components of the Chloroplast Protein Import Machinery", Science, 266:1007-1011 (Nov. 1994).

Kessler et al., "Identification of Two GTP-Binding Proteins in the Chloroplast Protein Import Machinery", Science, 266:1035-1039 (Nov. 1994).

Newhall et al., "Cross-Linking Analysis of the Outer Membrane Proteins of *Neisseria gonorrhoeae*", Infection and Immunity, 28(3):785-791 (Jun. 1980).

Swanson et al., "Studies on *Gonococcus* Infection, XII. Colony Color and Opacity Variants of *Gonococci*", Infection and Immunity, 19(1):320-331 (Jan. 1978).

Laemmli et al., "Cleavage of Structural Proteins During the Assembly of the Head of Bacteriophage T4", Nature, 227:680-685 (Aug. 1970).

Judd et al., "Purification of Outer Membrane Proteins of the Gram-Negative Bacterium *Neisseria gonorrhoeae*", Analytical Biochemistry, 173:307-316 (Sep. 1988).

Moore, "Preparation and Analysis of DNA", in *Current Protocols in Molecular Biology*, F.M. Ausubel et al., (eds), New York, John Wiley and Sons, Suuplement 25, 2.1.1-2.1.3 (1995).

Southern, "Detection of Specific Sequences Among DNA Fragments Separated by Gel Electrophoresis", J. Mol. Biol., 98:503-517 (Nov. 5, 1975).

Marchion et al., "Generation of Antiserum to Specific Epitopes", Molecular Biotechnology, 6:231-240 (Dec. 1996).

Manning et al., "Omp85 Proteins of *Neisseria gonorrhoeae* and *Neisseria meningitidis* are Similar to *Haemophilus influenzae* D-15-Ag and *Pasteurella multocida* Oma87", Microbial Pathogenesis, 25:11-21 (Jul. 1998).

Reschke et al., "Characterization of an 96 kDa Outer Membrane Protein of *Neisseria gonorrhoeae* Having Homology with the D15 Surface Protective Antigen of *Haemophilus influenzae*", in *Pathogenic Neisseria*, W. Zollinger et al. (eds), p. 44, NIH, Bethesda, MD (1996).

Cohen et al., "Mucosal Infection with *Neisseria gonorrhoeae*, Bacterial Adaptation and Mucosal Defenses", J. Clin. Invest., 89:1699-1705 (Jun. 1992).

Kaneko et al., "Sequence Analysis of the Genome of the Unicellular Cyanobacterium *synechocystis* sp. Strain PCC 6803. II. Sequence Determination of the Entire Genome and Assignment of Potential Protein-Coding Regions", DNA Research, 3:109-136 (Jun. 30, 1996).

Manning et al., "*Neisseria gonorrhoeae* Outer Membrane Protein (omp85) Gene, Complete cds", EMPRO Database Accession No. U81959 (Feb. 22, 1997).

Manning et al., "*Neisseria meningitidis* Outer Membrane Protein (omp85) Gene, Complete cds" EMPRO Database Accession No. AF021245 (Oct. 3, 1997).

Uhlen et al., "Gene Fusion Vectors Based on the Gene for *Staphylococcal* Protein A", Gene, 23(3):369-378 (Sep. 1983) (Abstract).

Houghton et al., "Relative Importance of Position and Individual Amino Acid Residues in Peptide Antigen-Antibody Interactions: Implications in the Mechanism of Antigenic Drift and Antigenic Shift", in *Vaccines*, pp. 21-25, F. Brown et al., (eds), Cold Spring Harbor Laboratory (1986).

Lewis et al., "Identification of an Iron-Regulated Outer Membrane Protein of *Neisseria meningitidis* Involved in the Utilization of Hemoglobin Complexed to Haptoglobin", J. Bacteriology, 177(5):1299-1306 (Mar. 1995).

Lewis et al., "Molecular Characterization of hpuAB, the Haemoglobin-Haptoglobin-Utilization Operon of *Neisseria meningitidis*", Molecular Microbiology, 23(4):737-749 (Feb. 1997).

Blasius et al., "Two Distinct Outer Membrane Serotype Subcomplexes of *Neisseria meningitidis* Serogroup A", Infection and Immunity, 58(6):2008-2010 (Jun. 1990).

Ferreiros et al., "Analysis of the Molecular Mass Heterogeneity of the Transferring Receptor of *Neisseria meningitidis* and Commensal *Neisseria*", FEMS Microbiology Letters, 83:247-254 (1991).

Dyer et al., "Isolation by Streptonigrin Enrichment and Characterization of a Transferrin-Specific Iron Uptake Mutant of *Neisseria meningitidis*", Microbial Pathogenesis, 3:351-363 (Nov. 1987).

Anderson et al., "Gonococcal Transferrin-Binding Protein 2 Facilitates but is not Essential for Transferrin Utilization", J. Bacteriology, 176(11):3162-3170 (Jun. 1994).

Legrain et al., "Cloning and Characterization of *Neisseria meningitidis* Genes Encoding the Transferrin-binding Proteins Tbp1 and Tbp2", Gene, 130:73-80 (Aug. 16, 1993).

Chen et al., "Identification and Purification of a Hemoglobin-Binding Outer Membrane Protein from *Neisseria gonorrhoeae*", Infection and Immunity, 64(12):5008-5014 (Dec. 1996).

Pelloquin et al., EMPRO Database Accession No. Y07891 (Jul. 1, 1997).

Richarme et al., "Membrane Potential Stimulated Binding of the Maltose-Binding Protein to Membrane Vesicles of *Escherichia coli*", Ann. Microbiol. (Paris), 133A(1):199-204 (Jan. 1982) (Abstract).

Lazar et al., "Transforming Growth Factor α: Mutation of Aspartic Acid 47 and Leucine 48 Results in Difference Biological Activities", Mol. Cell. Biol., 8:1247-1252 (Mar. 1988).

Ellis, "New Technologies for Making Vaccines", in *Vaccines*, Plotkin et al. (eds), WB Saunders Company, Philadelphia, PA, Chapter 29, pp. 568-575 (1988).

Rosenqvist et al, Human Antibody Responses to Meningococcal Outer Membrane Antigens After Three Doses of the Norwegian Group B Meningococcal Vaccine, Infection and Immunity, pp. 4642-4652, vol. 63, No. 12, (Dec. 1995).

Wedege et al, Immune Responses Against Major Outer Membrane Antigens of *Neisseria Meningitidis* in Vaccinees and Controls Who Contracted Meningococcal Disease During the Norwegian Serogroup B Protection Trial, Infection and Ummunity, pp. 3223-3231, vol. 66, No. 7, (Jul. 1998).

Yang et al, A 20-Kilodalton N-Terminal Fragment of the D15 Protein Contains a Protective Epitope(S) against *Haemophilus influenzae* Type a and Type b, Infection and Immunity, pp. 3349-3354, vol. 66, No. 7, (Jul. 1998).

Judd, R.C., Identification of Surface Epitopes of Neisserial Outer Membrane Protein 85, the Fourteenth International conference on Pathogenic *Neisseria*, Milwaukee, WI, (Sep. 5-10, 2004), [Power Point Presentation].

Makino, "Phase Variation of the Opacity Outer Membrane Protein Controls Invasion by *Neisseria gonorrhoeae* into Human Epithelial Cells", The EMBO Journal, 10(6):1307-1315, (Jun. 1991).

Duensing, "Vitronectin Mediates Internalization of *Neisseria gonorrhoeae* by Chinese Hamster Ovary Cells", Infection and Immunity, 65(3):964-970, (Mar. 1997).

De Vries et al, "Invasion of primary nasopharyngeal epithelial cells by *Neisseria meningitidis* is controlled by phase variation of multiple surface antigens", Infec Immun, 64(8):2998-3006 (Aug. 1996).

Stephens et al, "Attachment of pathogenic *Neisseria* to human mucosal surfaces: role in pathogenesis", Infection, 10(3):192-195 (1982).

Bhasin, et al. Infect. Immun., vol. 69, pp. 5031-5036, (Aug. 2001).

* cited by examiner

FIG. 2A

```
      TAG ATTTTACGTTTCGGAATGCAGTCTGAAACCGCATTCCGCACCACAAGAACTTACG
  1   ATGAAACTGAAACAGATTGCCTCCGCACTGATGATGTTGGGCATTTCCCCTTTGGCATTTGCCGACTTCACCATC
      M   K   L   K   Q   I   A   S   A   L   M   M   L   G   I   S   P   L   A   F   A ▲ D   F   T   I
 76   CAAGACATCCGTGTCGAAGGCTTGCAGCCGAGCACCGTATTCAACTACCTGCCCGTCAAAGTCGGC
      Q   D   I   R   V   E   G   L   Q   P   S   T   V   F   N   Y   L   P   V   K   V   G
151   GACACCTACAACGACACACACGGCAGTGCCATCATCAAAAGCCTGTACGCCACCGGTTTCTTTGACGACGTACGA
      D   T   Y   N   D   T   H   G   S   A   I   I   K   S   L   Y   A   T   G   F   F   D   D   V   R
226   GTCGAAACTGCGGACGGGCTGCTTCTGCTTGTATCGAACCTCGGCTCGCTCAACATCACCGGC
      V   E   T   A   D   G   L   L   L   L   V   I   C   P   T   I   G   S   L   N   I   T   G
301   GCCAAAATGCTGCAGAACGACGCCATCAAGAAAAACCTGTTCGGCAGTCGCAATACTTTAAT
      A   K   M   L   Q   N   D   A   I   K   K   N   L   E   S   F   G   L   A   Q   S   Q   Y   F   N
376   CAGGCGACACTCAACCAGGCAGTCGCCGCGCAAACTCGACGATTGACGAGGCAAATCCGCCAAA
      Q   A   T   L   N   Q   A   V   A   G   L   K   E   E   Y   L   G   R   G   K   L   N   I   Q   I
451   ACGCCCAAAGTAACCAAACTCGCCGCAACATCGACACTCGACACCGCAAACTGATGTCGCTGACCGAA
      T   P   K   V   T   K   L   A   R   N   R   V   D   I   D   I   T   I   D   E   G   K   S   A   K
526   ATCACCGACATCGAATTTGAAGGCAACCAAGTCTATTCCGACCGGTTCGACCGCAAGCTGATGCGCCAGATGTCGCTGACCGAA
      I   T   D   I   E   F   E   G   N   Q   V   Y   S   D   R   K   L   M   R   Q   M   S   L   T   E
601   GGCGGCATTTGGACACTGCGCTCCGACCGGTTCCTCGATATCCTCGATATCCTCGATACCGAAGAGACAAA
      G   G   I   W   T   L   T   R   S   D   R   F   D   R   Q   K   F   A   Q   D   M   E   K   V
676   ACCGACTTCTACCAGAACAACGGCTACTTCGATTTCCGTATCCTCGATACCGACATCCAAACCAACGAAGACAAA
      T   D   F   Y   Q   N   N   G   Y   F   D   F   R   I   L   D   T   D   I   Q   T   N   E   D   K
751   ACCAGGCAGACCATCAAAATCACCGTCCACGAAGGCGGACGTTTCCGCTTGACCATGAAGCCCGGACGCTTCTGAAGGCGAC
      T   R   Q   T   I   K   I   T   V   H   E   G   G   R   F   R   W   G   K   V   S   I   E   G   D
826   ACCAACGAAGTCCCCAAGGCCGAACTGGAAAAACTGCTGACCATGAAGCCCGGCAAATGGTACGAACGCCAGCAG
      T   N   E   V   P   K   A   E   L   E   K   L   L   T   M   K   P   G   K   W   Y   E   R   Q   Q
901   ATGACCGCCGTTTTGGGTGTGAGATTCAGAATTCAGAATACGCCATACAGCCAGGCTACAGCGAAATCAGCGTACAG
      M   T   A   V   L   G   E   I   Q   N   R   M   G   S   A   G   Y   A   Y   S   E   I   S   V   Q
```

```
 976  CCGCTGCCGAACGCCGGAACCAAAACCGTCGATTTCGTCCTGCACATCGAACCGGGCAGAAAAATCTACGTCAAC
      P  L  P  N  A  G  T  K  T  V  D  F  V  L  H  I  E  P  G  R  K  I  Y  V  N   350
1051  GAAATCCACATCACCGGCAACAACAAAACCCGCGACGAAGTCGTCCGCGAATTGCGCCAAATGGAATCCGCG
      E  I  H  I  T  G  N  N  K  T  R  D  E  V  V  R  R  E  L  R  Q  M  E  S  A   375
1126  CCTTACGACACCTCCAAGCTGCAACGCTCCAAAGAGCGCGTCGAGCTTTGGCTACTTCGACAACGTACAGTTT
      P  Y  D  T  S  K  L  Q  R  S  K  E  R  V  E  L  L  G  Y  F  D  N  V  Q  F   400
1201  GATGCCGTCCCGCTTGCCGGTACGCCCGACAAAGTCGATTGAACATGAGCCTGACCGAACGTTCCACCGGCTCG
      D  A  V  P  L  A  G  T  P  D  K  V  D  L  N  M  S  L  T  E  R  S  T  G  S   425
1276  CTCGACTTGAGCGCGGGTTGGGTTCAGGATACCGGCCTTGTCATGTCCGCAGGATCGCAGGACAACCTGTTC
      L  D  L  S  A  G  W  V  Q  D  T  G  L  V  M  S  A  G  V  S  Q  D  N  L  F   450
1351  GGTACGGGCAAGTCGGCCGCCGCTCTGCGCGAAGCAAAACGCTCAACGCTTCGGCTCGTCGTTTACCGAC
      G  T  G  K  S  A  A  L  R  A  S  R  K  T  T  L  N  G  S  L  S  F  T  D   475
1426  CCGTACTTCACGGCAGACGGGTCAGCGCTACGATATTTACGGGGCTAAGGATGGGTATCCCGTTACCGAATACGAC
      P  Y  F  T  A  D  G  V  S  L  G  Y  D  I  Y  G  K  A  F  D  P  R  K  A  S   500
1501  ACCAGCGTCAAACAATATATAAAACCACCGGCCGGCGGTCAACACCGTCACAACACCCAAACGCTATGCCGAC
      T  S  V  K  Q  Y  K  T  T  T  A  G  G  G  V  R  M  G  I  P  V  T  E  Y  D   525
1576  CGCGTCAATTTCGGGCTGGCGCGCCGAACACCTGACCGTCACAACACCGTCTTCAAAGCACCCAAAGCCTATGCCGAC
      R  V  N  F  G  L  A  E  H  L  T  V  N  T  Y  N  K  A  P  K  R  Y  A  D   550
1651  TTTATCAAACAATACGGCAAAACGGACGGCGCAGACGGCGCAGCTTCAAAGGCCTGCTGTACAAAGGCACTGTCGGC
      F  I  K  Q  Y  G  K  T  D  G  A  D  G  S  F  K  G  L  L  Y  K  G  T  V  G   575
1726  TGGGGGCGCAACAAGACCGACAGCGCCTTATGGCCGACCAGCGGCTACCTGACCGGTGTAAATGCCGAAATCGCC
      W  G  R  N  K  T  D  S  A  L  W  P  T  R  G  Y  L  T  G  V  N  A  E  I  A   600
1801  CTGCCCCGGCAGACAACTGCAATACTACTCCGCACACCGAAACCTGTTCTTCCCCTTAAGCAAAACCTTC
      L  P  G  S  K  L  Q  Y  S  A  T  H  N  Q  T  W  F  F  P  L  S  K  T  F   625
1876  ACGCTGATGCTCGGCGGCGAAGTCGGCATTGCGGGCGGCTACGGCAGAACCAAAGAAATCCCCTTCTTTGAAAAC
      T  L  M  L  G  G  E  V  G  I  A  G  G  Y  G  R  T  K  E  I  P  F  F  E  N   650
1951  TTCTACGGCGGGCTGGGTTCGGTGCGCGGCTACGAAAGCGGCACGCTCGGCCCGAAAGTGTATGACGAATAC
      F  Y  G  G  L  G  S  V  R  G  Y  E  S  G  T  L  G  P  K  V  Y  D  E  Y   675
```

FIG. 2C

```
2026  GGCGAAAAATCAGCTACGGCGGCAACAAAAAGCCAACGTCTCCGCCGAGCTGCTCTTCCCGATGCCGGTGCG   700
       G  E  K  I  S  Y  G  G  N  K  K  A  N  V  S  A  E  L  L  F  P  M  P  G  A
2101  AAAGACGGCACGCGTCCGTCCGAGCCGTGTTGCCGACGCAGGCGTGTGGGACGGCAGAACCTATACCGCC    725
       K  D  A  R  T  V  R  L  S  L  F  A  D  A  G  S  V  W  D  G  R  T  Y  T  A
2176  GCCGAAAACGGGTAACAACAAATCGGTTTACTCGGAAAAACGGCATAAATCCACCTTTACCAACGAATTGCGCTAT
       A  E  N  G  N  N  K  S  V  Y  S  E  N  A  H  K  S  T  F  T  N  E  L  R  Y
2251  TCCGCCGGCGGGTTACCTGGCTCTCTGCCTTTGGGCCCGATGAAATTCATCTACGCCCTACCCGCTGAAGAAA    750
       S  A  G  G  A  V  T  W  L  S  P  L  G  P  M  K  F  I  Y  A  Y  P  L  K  K
2326  AAACCGGAAGACGAAATCCAAGCTTCCATTCCAGCTCGGCACGACGTTC TAA CCCGCAAATGCCGTCTGAAG  775
       K  P  E  D  E  I  Q  R  F  Q  F  Q  L  G  T  T  F                          792
2399  CCCTTCAGACGGCATTTCGCGGCAACATCCGAAGGAGTTTTACC ATG
```

FIG. 5

```
MKLKQIASALMMLGISPLAFADFTIQDIRVEGLQRTEPSTVFNYLPVKVGDTYNDTHGSAIIKSLYATGFFDDVRVETAD        80

GQLLTVIERPTIGSLNITGAKMLQNDAIKKNLESFGLAQSQYFNQATLNQAVAGLKEEYLGRGKLNIQITPKVTKLARN       160
 L           VC

RVDIDITIDEGKSAKITDIEFEGNQVYSDRKLMRQMSLTEGGIWTWLTRSNQFNEQKFAQDMEKVTDFYQNNGYFDFRIL       240
                                              DR DR

DTDIQTNEDKTKQTIKITVHEGGRFRWGKVSIEGDTNEVPKAELEKLLTMKPGKWYERQQMTAVLGEIQNRMGSAGYAYS       320
          R

EISVQPLPNAETKTVDFVLHIEPGRKIYVNEIHITGNNKTRDEVVRRELRQMESAPYDTSKLQRSKERVELLGYEDNVQF       400
              G

DAVPLAGTPDKVDLNMSLTERSTGSLDLSAGWVQDTGLVMSAGVSQDNLFGTGKSAALRASRSKTTLNGSLSFTDPYFTA       480

DGVSLGYDVYGKAFDPRKASTSIKQYKTTAGAGIRMSVPVTEYDRVNFGLVAEHLTVNTYNKAPKHYADFIKKYGKTDG       560
      I         V                  G V GI           A          R      Q

TDGSFKGWLYKGTVGWGRNKTDSALWPTRGYLTGVNAEIALPGSKLQYYSATHNQTWFFPLSKTFTLMLGGEVGIAGGYG       640
A         L

RTKEIPFENFYGGLGSVRGYESGTLGPKVYDEYGEKISYGGNKANVSAELLFPMPGAKDARTVRLSLFADAGSVWDG       720
                                                I

KTYDDNSSATGGRVQNIYGAGNTHKSTFTNELRYSAGGAVTWLSPLGPMKFRYAYPLKKKPEDEIQRFQFQLGTTE       797
R  ***TAAEN NN*KSV *SE A
```

OMP85 PROTEINS OF *NEISSERIA GONORRHOEAE* AND *NEISSERIA MENINGITIDIS*, COMPOSITIONS CONTAINING SAME AND METHODS OF USE THEREOF

CROSS-REFERENCE TO RELATED APPLICATIONS

This application is a continuation of U.S. patent application Ser. No. 09/994,192, filed Nov. 26, 2001, now U.S. Pat. No. 6,610,306, which is a continuation of U.S. patent application Ser. No. 09/177,039, filed Oct. 22, 1998, now abandoned.

This invention was made with government support under grant Nos. AI21235 and AI37777 awarded by the National Institutes of Health. The government has certain rights in the invention.

BACKGROUND OF THE INVENTION

This invention relates generally to the cloning and identification of novel outer membrane proteins of several strains of *Neisseria*, and more specifically to proteins useful in the prevention, therapy and/or diagnosis of infection and diseases in mammals caused by these strains.

The pathogenic *Neisseriae* cause several important non-symptomatic infections and symptomatic diseases in humans. *Neisseria gonorrhoeae* is the agent of non-symptomatic gonococcal infection or symptomatic disease, i.e., gonorrhea. *Neisseria meningitidis* is the agent of a rapidly progressive spinal meningitis, which may also have a non-symptomatic infective stage. The surfaces of such pathogens provide crucial interfaces for interactions between the pathogen and the host. Many bacterial virulence factors are outer membrane proteins, and surface exposed proteins are the primary targets recognized and attacked by the host's immune system. Thus, the role of outer membrane proteins is of particular importance in understanding the pathogenesis of these organisms. The most abundant and immunodominant outer membrane proteins of the pathogenic *Neisseriae* have been studied extensively (Sparling P. F. et al, *Clin. Invest.*, 89: 1699-1705 (1992)). For example, it is known that the immunodominant components of the gonococcal surface are antigenically variant, suggesting that this organism is capable of adapting to varying host environments while avoiding host immune responses. Although the major gonococcal surface proteins have been extensively studied, little is known about less abundant proteins and their contributions to pathogenesis.

Two-dimensional electrophoresis (IEF and SDS-PAGE) of labeled, e.g., radioiodinated or biotinylated, gonococcal surface proteins suggested that numerous (>20) of the less abundant gonococcal outer membrane proteins remained uncharacterized (unpublished observations). Among these might be proteins which play an important role in infection.

For example, surface-exposed outer membrane proteins of other microorganisms, e.g., *Haemophilus influenzae* D15 surface antigen (D-15-Ag) and the *Pasteurella multocida* Oma87, have been found to be useful in eliciting antibodies that were protective against infectious challenge in animal models. The Omp85-like D-15-Ag was conserved in both non-typeable and typeable strains of *H. influenzae* and was recognized by convalescent patient sera; affinity-purified anti-D-15-Ag serum was protective in the rat pup model (Thomas, W. R., et al, *Infect. Immun.*, 58:1909-1913 (1990); Flack, F. S. et al, *Gene*, 156:97-99 (1995)]). *H. influenzae* serotypes a-f, nontypeable *H. influenzae* and *Haemophilus parainfluenzae* all expressed proteins similar to the D-15-Ag, as demonstrated by immunoblot analysis. Antibodies to recombinant D-15-Ag protected against *H. influenzae* type b and type a bacteremia in the infant rat model (Loosmore, S. M. et al, *Infect. Immun.*, 65:3701-3707 (1997)).

Like *H. influenzae* D-15-Ag, the Oma87 of *P. multocida* was highly conserved among strains and was recognized by protective antibody; it was present in all 16 serotypes of *P. multocida* and was recognized by convalescent animal sera. Antibodies raised to recombinant Oma87 were protective against homologous challenge in the mouse model (Ruffolo, C. G. et al., *Infect. Immun.*, 64:3161-3167 (1996)). Despite the several publications describing the immunological properties of D-15-Ag and Oma87, the function of these proteins remains unknown.

There remains a need in the art for the development of proteins from *Neisseriae* which are useful in research, diagnosis and treatment of the infections, especially non-symptomatic infections, and the diseases caused by these pathogens.

SUMMARY OF THE INVENTION

In one aspect, the invention provides an isolated outer membrane protein of *N. gonorrhoeae* having an apparent molecular weight of 85 kDa and characterized by an amino acid sequence of SEQ ID NO: 2, a fragment, an analog or a homolog thereof.

In another aspect, the invention provides a nucleic acid sequence encoding the Omp85 of *N. gonorrhoeae* or a fragment thereof.

In still another aspect, the invention provides a nucleic acid molecule comprising a nucleic acid sequence encoding the Omp85 of *N. gonorrhoeae* or a fragment thereof under the control of suitable regulatory sequences which direct expression of said Omp85 protein or fragment in a selected host cell.

In yet a further aspect, the invention provides a host cell transformed with the above described nucleic acid molecule.

In still a further aspect, the invention provides a method of recombinantly expressing the Omp85 of *N. gonorrhoeae* or a fragment thereof comprising the steps of culturing a recombinant host cell transformed with a nucleic acid sequence encoding said protein or fragment under conditions which permit expression of said protein or peptide.

In another aspect, the invention provides a method for preparing an Omp85 protein of *N. gonorrhoeae* or fragment thereof comprising chemically synthesizing said protein or fragment.

In yet another aspect, the invention provides a diagnostic reagent comprising a nucleic acid sequence encoding Omp85 of *N. gonorrhoeae*, isolated from cellular materials with which it is naturally associated, a sequence complementary thereto, a fragment thereof, a sequence which hybridizes thereto under stringent conditions, an allelic variant thereof, a mutant thereof, or a sequence encoding Omp85 or a fragment thereof fused to a sequence encoding a second protein, and a detectable label which is associated with said sequence.

In still another aspect, the invention provides an isolated antibody which is directed against Omp85 of *N. gonorrhoeae* or a fragment thereof.

In a further aspect, the invention provides an anti-idiotype antibody specific for the antibody described above.

In another aspect, the invention provides a diagnostic reagent comprising the antibody or anti-idiotype antibody described above and a detectable label.

In yet another aspect, the invention provides a vaccine composition comprising an effective amount of a Omp85 protein of *N. gonorrhoeae*, a fusion protein or fragment thereof and a pharmaceutically acceptable carrier. This composition can also include at least one other antigen or fragment thereof.

In another aspect, the invention provides a vaccine composition comprising an effective amount of a nucleic acid sequence encoding the Omp85 protein of *N. gonorrhoeae*, a fusion protein, or a fragment thereof and a suitable nucleic acid delivery vehicle. This vaccine composition may also be polyvalent.

In still a further aspect, the invention provides a method of vaccinating a human or animal against gonococcal infection or disease comprising administering to said human or animal a composition comprising an effective amount of at least one of the compositions described above.

Another aspect of the present invention includes a method for diagnosing gonococcal infection or disease in a human or animal comprising the steps of contacting an Omp85 antigen optionally associated with a detectable label or a homolog thereof with a biological sample from a human subject to be diagnosed, wherein the presence of naturally occurring antibodies to *N. gonorrhoeae* in said sample permits the formation of an antigen-antibody complex, and analyzing said sample for the presence of said complex, which indicates infection with *N. gonorrhoeae*.

Still another aspect of the invention provides a method for diagnosing gonococcal infection or disease in a human or animal comprising the steps of: contacting an Omp85 antibody, optionally associated with a detectable label, with a biological sample from a human subject to be diagnosed, wherein the presence of naturally occurring *N. gonorrhoeae* Omp85 in said sample permits the formation of an antigen-antibody complex, and analyzing said sample for the presence of said complex, which indicates infection with *N. gonorrhoeae*.

Yet a further aspect of the invention provides a method for diagnosing gonococcal infection or disease in a human or animal comprising the steps of: employing a nucleic acid sequence encoding all or a portion of an Omp85 antigen or an Omp85 antibody, optionally associated with a detectable label, as a probe which, when in contact with a biological sample from a human subject to be diagnosed, enables detection of infection by hybridization or amplification of nucleic acid sequences of *N. gonorrhoeae* Omp85 in said sample.

Yet a further aspect of the invention includes a therapeutic composition useful in treating humans or animals with non-symptomatic gonococcal infection or symptomatic disease comprising at least one anti-*N. gonorrhoeae* Omp85 antibody and a suitable pharmaceutical carrier.

In still another aspect, the invention includes a method for treating non-symptomatic gonococcal infection or symptomatic disease in a mammalian host comprising administering an effective amount of the therapeutic composition described above.

In yet another aspect, the invention provides a kit for diagnosing infection with *N. gonorrhoeae* in a human or animal comprising an Omp85 protein or fragment thereof or an anti-Omp85 antibody or a nucleic acid sequence encoding the protein or antibody as described above.

In another aspect, the invention provides a method of identifying compounds which specifically bind to Omp85 of *N. gonorrhoeae* or a fragment thereof, comprising the steps of contacting said Omp85 protein or fragment with a test compound to permit binding of the test compound to Omp85; and determining the amount of test compound which is bound to Omp85.

In still another aspect, the invention provides a compound identified by the above method.

In one aspect, the invention provides an isolated outer membrane protein of *N. meningitidis* having an apparent molecular weight of 85 kDa and characterized by an amino acid sequence of SEQ ID NO: 4, a fragment, an analog or a homolog thereof.

In another aspect, the invention provides a nucleic acid sequence encoding the Omp85 of *N. meningitidis* or a fragment thereof.

In still another aspect, the invention provides a nucleic acid molecule comprising a nucleic acid sequence encoding the Omp85 of *N. meningitidis* or a fragment thereof under the control of suitable regulatory sequences which direct expression of said Omp 85 or fragment in a selected host cell.

In yet a further aspect, the invention provides a host cell transformed with the above described nucleic acid molecule.

In still a further aspect, the invention provides a method of recombinantly expressing the Omp85 of *N. meningitidis* or a fragment thereof comprising the steps of culturing a recombinant host cell transformed with a nucleic acid sequence encoding said protein or fragment under conditions which permit expression of said protein or peptide.

In another aspect, the invention provides a method for preparing an Omp85 protein of *N. meningitidis* or fragment thereof comprising chemically synthesizing said protein or fragment.

In yet another aspect, the invention provides a diagnostic reagent comprising a nucleic acid sequence encoding Omp85 of *N. meningitidis*, isolated from cellular materials with which it is naturally associated, a sequence complementary thereto, a fragment thereof, a sequence which hybridizes thereto under stringent conditions, an allelic variant thereof, a mutant thereof, or a sequence encoding Omp85 or a fragment thereof fused to a sequence encoding a second protein, and a detectable label which is associated with said sequence.

In still another aspect, the invention provides an isolated antibody which is directed against Omp85 of *N. meningitidis* or a fragment thereof.

In a further aspect, the invention provides an anti-idiotype antibody specific for the antibody described above.

In another aspect, the invention provides a diagnostic reagent comprising the antibody or anti-idiotype antibody described above and a detectable label.

In yet another aspect, the invention provides a vaccine composition comprising an effective amount of a Omp85 protein of *N. meningitidis*, a fusion protein or fragment thereof and a pharmaceutically acceptable carrier. This composition can also include at least one other antigen or fragment thereof.

In another aspect, the invention provides a vaccine composition comprising an effective amount of a nucleic acid sequence encoding the Omp85 protein of *N. meningitidis*, a fusion protein, or a fragment thereof and a suitable nucleic acid delivery vehicle. This vaccine composition may also be polyvalent.

In still a further aspect, the invention provides a method of vaccinating a human or animal against non-symptomatic meningococcal infection and symptomatic disease comprising administering to said human or animal a composition comprising an effective amount of at least one of the compositions described above in either a pharmaceutically acceptable carrier or a nucleic acid delivery system.

Another aspect of the present invention includes a method for diagnosing non-symptomatic gonococcal infection or symptomatic disease in a human or animal comprising the steps of contacting an Omp85 antigen optionally associated with a detectable label or a homolog thereof with a biological sample from a human subject to be diagnosed, wherein the presence of naturally occurring antibodies to *N. meningitidis* in said sample permits the formation of an antigen-antibody complex, and analyzing said sample for the presence of said complex, which indicates infection with *N. meningitidis*.

Still another aspect of the invention provides a method for diagnosing non-symptomatic meningococcal infection and symptomatic disease in a human or animal comprising the steps of: contacting an Omp85 antibody, optionally associated with a detectable label, with a biological sample from a human subject to be diagnosed, wherein the presence of naturally occurring *N. meningitidis* Omp85 in said sample permits the formation of an antigen-antibody complex, and analyzing said sample for the presence of said complex, which indicates infection with *N. meningitidis*.

Yet a further aspect of the invention provides a method for diagnosing non-symptomatic meningococcal infection and symptomatic disease in a human or animal comprising the steps of: employing a nucleic acid sequence encoding all or a portion of an Omp85 antigen or an Omp85 antibody, optionally associated with a detectable label, as a probe which, when in contact with a biological sample from a human subject to be diagnosed, enables detection of infection by hybridization or amplification of nucleic acid sequences of *N. meningitidis* Omp85 in said sample.

Yet a further aspect of the invention includes a therapeutic composition useful in treating humans or animals with non-symptomatic meningococcal infection and symptomatic disease comprising at least one anti-*N. meningitidis* Omp85 antibody and a suitable pharmaceutical carrier.

In still another aspect, the invention includes a method for treating non-symptomatic meningococcal infection and symptomatic disease in a mammalian host comprising administering an effective amount of the therapeutic composition described above.

In yet another aspect, the invention provides a kit for diagnosing infection with *N. meningitidis* in a human or animal comprising an Omp85 protein or fragment thereof or an anti-Omp85 antibody or a nucleic acid sequence encoding the Omp85 protein or antibody, as described above.

In another aspect, the invention provides a method of identifying compounds which specifically bind to Omp85 of *N. meningitidis* or a fragment thereof, comprising the steps of contacting said Omp85 protein or fragment with a test compound to permit binding of the test compound to Omp85; and determining the amount of test compound which is bound to Omp85.

In still another aspect, the invention provides a compound identified by the above method.

Other aspects and advantages of the present invention are described further in the following detailed description of the preferred embodiments thereof, reference being made to the accompanying figures.

BRIEF DESCRIPTION OF THE DRAWINGS

FIGS. 2A-2C illustrate the DNA sequence encoding an open reading frame of the *N. gonorrhoeae* omp85 (SEQ ID NO: 1) and the corresponding deduced amino acid sequence of Omp85 (Genbank accession #U81959) (SEQ ID NO: 2), which is preceded by an untranslated 5' sequence (SEQ ID NO: 7), and followed by an untranslated 3' sequence (SEQ ID NO: 8). The nucleotide sequence begins with the termination codon of a preceding open reading frame (ORF) that is similar to that of the *H. influenzae* hypothetical protein HI0918 and ends with the initiation codon of a downstream gene similar to ompH of *S. typhimurium* (Kosk P. et al, *J. Biol. Chem.*, 264: 18973-18980 (1989)). The nucleotides of the omp85 open reading frame are numbered on the left. A ribosome binding site (underlined) precedes the initiation codon of the omp85 ORF. The omp85 ORF was preceded and followed by rho-independent transcriptional termination sequences (indicated by lines with arrows). The Omp85 precursor polypeptide was composed of 792 amino acids. The amino acid sequence is numbered on the right. A putative signal peptide cleavage site was identified (indicated by arrowhead) (Von Heijne, G., *Nucl. Acids Res.*, 14:4683-4690 (1986)). Cleavage at this site would produce a mature protein having a predicted molecular weight of 85,842 Da.

FIG. 5 illustrates the amino acid sequence of N meningitidis Omp85 (Genbank accession #AF021045) (SEQ ID NO: 4) compared to that of *N. gonorrhoeae* Omp85 (SEQ ID NO: 2). On the top line is the *N. meningitidis* Omp85 amino acid sequence. Below it are the amino acids that are different in the *N. gonorrhoeae* Omp85. Amino acids that are absent in the gonococcal Omp85 are indicated by stars. Amino acids that are identical in the Omp85 homologs of *N. meningitidis, N. gonorrhoeae, H. influenzae* (D-15-Ag) and *P. multocida* (Oma87) are underlined. The amino acids of the meningococcal Omp85 are numbered on the right.

*Neisseriae* (relationship areas A, B, C, and D) and related Gram negative bacteria: *N. gonorrhoeae* FA19 (A), *Neisseria pharyngis* (A), *Neisseria cinerea* (A), *Neisseria lactamica* (B), *Neisseria mucosae* (B), *Neisseria flavescens* (C), *Neisseria animalis* (C), *Neisseria denitrificans* (C), *Moraxella catarrhalis* (D), *Klebsiella pneumoniae, Pseudomonas aeruginosa*, and *N. meningitidis* HH (A), as described in Example 7. *E. coli* DH5α and *E coli* DH5α/pOmp85, were used as negative and positive controls. Prestained molecular mass markers (MW) were indicated in kDa.

Figures 7A, 7B:
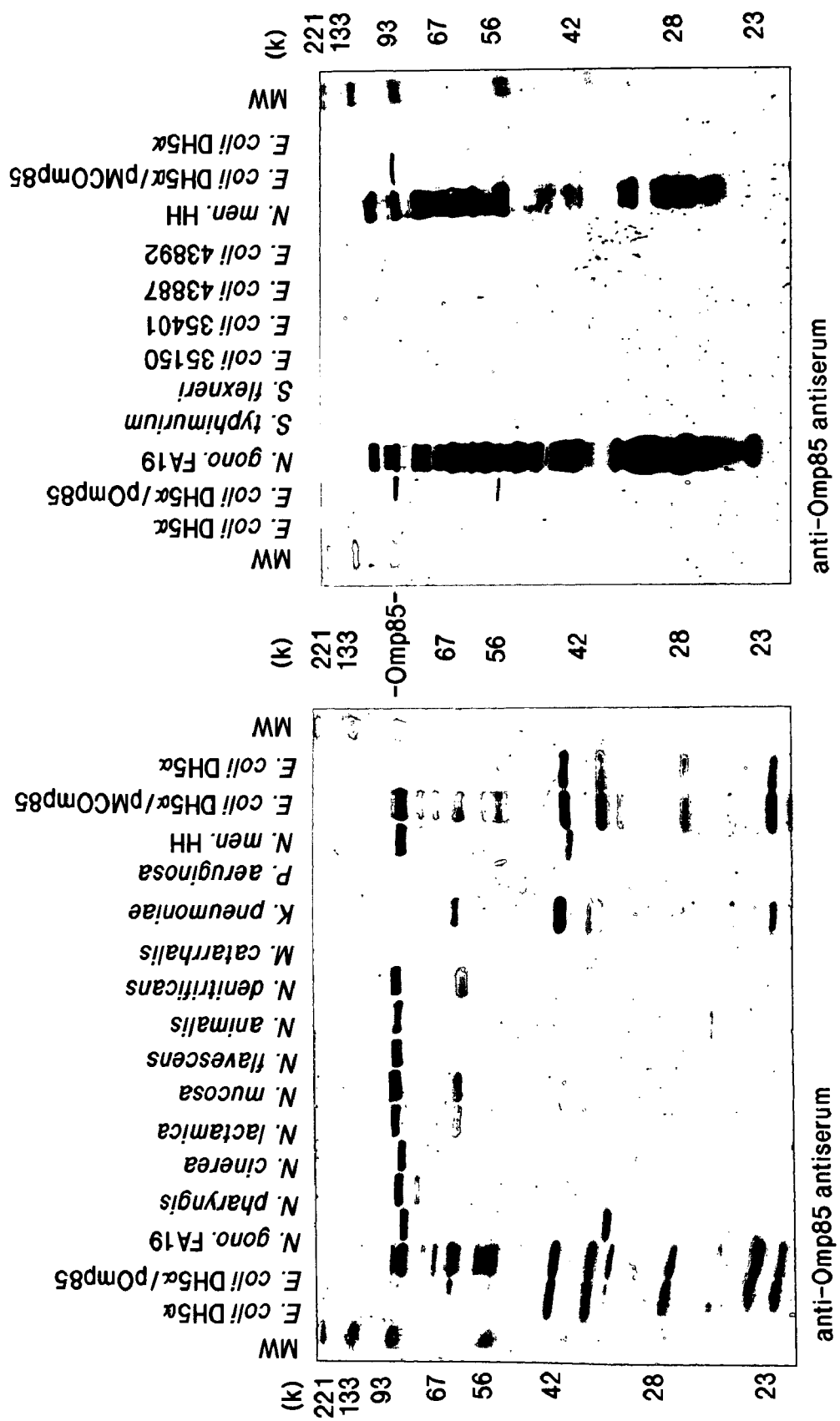
FIG. 7A is a photograph of a Western blot that illustrates the distribution of Omp85 in pathogenic and commensal

FIG. 7B is a photograph of a Western blot that illustrates the distribution of Omp85 in *N. gonorrhoeae* FA19, *Salmonella typhimurium, Shigella flexneri, E. coli* strains 35150 (enterohemorrhagic-EHEC), 35401 (enterotoxigenic-ETEC), 43887 (enteropathogenic-EPEC), 43892 (enteroinvasive-EIEC) and *N. meningitidis*, as described in Example 7. *E. coli* DH5α and *E. coli* DH5α/pOmp85 were used as negative and positive controls. Prestained molecular mass markers (MW) were indicated in kDa.

Figure 8:
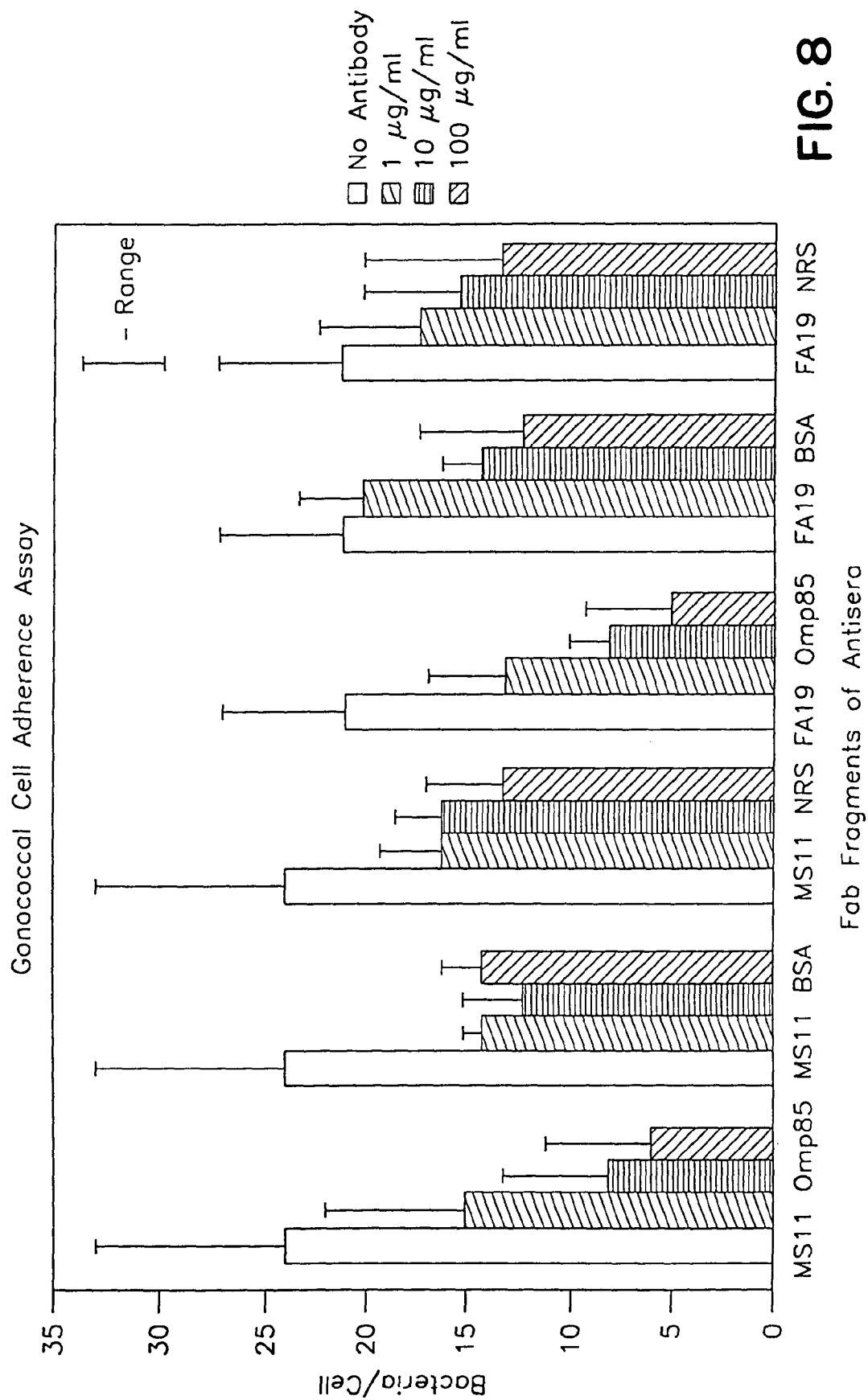

FIG. 8 is a bar graph showing the results of a gonococcal cell adherence assay performed with no antibody (black bars), and with Fab fragments prepared from antisera to: MS11 Omp85, MS11 hyperimmune sera to bovine serum albumin (MS11BSA), MS11 hyperimmune serum to normal rabbit serum (MS11NRS), FA19 Omp85, FA19BSA and FA19NRS at concentrations of 1, 10 and 100 µg/ml (see key). The assay was performed as described in Example 8.

DETAILED DESCRIPTION OF THE INVENTION

The present invention provides novel, characterized, outer surface membrane proteins, referred to as Omp85, from *N. gonorrhoeae* and *N. meningitidis*. These novel antigens, fragments thereof, antibodies developed thereto, the nucleic acid sequences encoding same, and the use of such antigens, antibodies and nucleic acid sequences provide diagnostic, therapeutic and prophylactic compositions and methods for the treatment or prevention of gonococcal and meningococcal infections, particularly non-symptomatic infections, and diseases.

I. The Omp85 Antigens of the Invention

To identify the previously uncharacterized *N. gonorrhoeae* outer membrane proteins, an *N. gonorrhoeae* genomic library was screened with an antiserum raised against purified isolated gonococcal outer membranes. The gonococcal gene, omp85, was identified that encodes a 792 amino acid outer membrane protein, Omp85, of *N. gonorrhoeae* having an apparent molecular weight of 85 kDa and characterized by the amino acid sequence of FIGS. 2A-2C and SEQ ID NO: 2. Omp85 has a typical signal peptide and a carboxyl-terminal phenylalanine characteristic of outer membrane proteins. Southern analysis demonstrated that the omp85 gene was present as a single copy in *N. gonorrhoeae* and *N. meningitidis*. PCR amplification was used to obtain a clone of the *N. meningitidis* omp85 homolog. The genes encoding the *N. gonorrhoeae* and *N. meningitidis* Omp85 proteins have been cloned and sequenced. The omp85 gene and its product in both *N. gonorrhoeae* and *N. meningitidis* are characterized in FIGS. 2 and 5 below (SEQ ID NOS: 1-4).

The nucleic acid sequences encoding the Omp85 proteins and the structures of the proteins themselves are described below. Where in this specification, protein and/or DNA sequences are defined by their percent homologies or identities to identified sequences, the algorithms used to calculate the percent identities or percent similarities include the following: the Smith-Waterman algorithm (J. F. Collins et al, 1988, *Comput. Appl. Biosci.*, 4:67-72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417), and the BLAST and FASTA programs (E. G. Shpaer et al, *Genomics*, 38:179-191 (1996)), including the BLAST2 program (S. D. Altschul et al, *J. Mol. Biol.*, 215:403-407 (1990)). These references are incorporated herein by reference.

A. Nucleic Acid Sequences

The present invention provides bacterial nucleic acid sequences encoding omp85 sequences of *N. gonorrhoeae* and *N. meningitidis*. The nucleic acid sequences of this invention are isolated from cellular materials with which they are naturally associated. The DNA sequence of the *N. gonorrhoeae* omp85 (SEQ ID NO: 1) and the corresponding deduced amino acid sequence of Omp85 (Genbank accession #U81959) (SEQ ID NO: 2) were obtained as described in Example 2 and in FIGS. 2A-2C. The nucleotide sequence begins with the termination codon of a preceding ORF that is similar to that of the *H. influenzae* hypothetical protein HI10918 and ends with the initiation codon of a downstream gene similar to ompH of *S. typhimurium* [(Kosk P. et al, *J. Biol. Chem.*, 264: 18973-18980 (1989)]). A ribosome binding site precedes the initiation codon of the omp85 ORF. The omp85 ORF was preceded and followed by rho-independent transcriptional termination sequences. The Omp85 precursor polypeptide was composed of 792 amino acids. A putative signal peptide cleavage site was identified (indicated by arrowhead) (Von Heijne, G., *Nucl Acids Res.*, 14:4683-4690 (1986)). Cleavage at this site produces a mature protein having a predicted molecular weight of 85,842 Da.

The DNA sequence of the *N. meningitidis* omp85 (SEQ ID NO: 3) and the corresponding deduced amino acid sequence of Omp85 (Genbank accession #AF021045) (SEQ ID NO: 4) were obtained as described in Example 3. FIG. 5 shows the comparison between the sequences of the two Omp85 proteins, as well as the similarities between the Omp85 homologs of *N. meningitidis, N. gonorrhoeae, H. influenzae* (D-15-Ag) and *P. multocida* (Oma87).

In addition to the full-length nucleic acid sequences encoding the Omp85 proteins provided herein, the specification also includes fragments of these omp85 genes. Preferably, such fragments are characterized by encoding a biologically active portion of Omp85, e.g., an epitope. Alternatively, other non-epitopic fragments may be useful as probes in diagnostic or research use. Generally, these oligonucleotide fragments are at least 10, or at least 15 consecutive nucleotides in length. However, oligonucleotide fragments of varying sizes may be selected as desired. Such fragments may be used for such purposes as performing polymerase chain reaction (PCR), e.g., on a biopsied tissue sample. For example, useful fragments of omp85 DNA and corresponding sequences comprise sequences occurring between nucleotides 2161 through 2208 of SEQ ID NO: 1 and nucleotides 2161 and 2218 of SEQ ID NO: 3. Other useful fragments may be readily obtained by one of skill in the art by resort to conventional DNA sequencing techniques applied to the sequences disclosed herein.

The DNA sequences of SEQ ID NOS: 1 and 3 permit one of skill in the art to readily obtain the corresponding antisense strands of these DNA sequences. Further, using known techniques, one of skill in the art can readily obtain additional genomic and cDNA sequences which flank the illustrated DNA sequences or the corresponding RNA sequences, as desired. Similarly the availability of SEQ ID NOS: 1 and 3 of this invention permits one of skill in the art to obtain other species Omp85 analogs, and fragments thereof, by use of the nucleic acid sequences of this invention as probes in a conventional technique, e.g., polymerase chain reaction. Allelic variants of these sequences within a species (i.e., sequences containing some individual nucleotide differences from a more commonly occurring sequence within a species, but which nevertheless encode the same protein or a protein with the same function) such as other variants of Omp85 (SEQ ID NOS: 2 and 4) may also be readily obtained given the knowledge of these nucleic acid sequences provided by this invention.

The present invention further encompasses nucleic acid sequences capable of hybridizing under stringent conditions (see, J. Sambrook et al, *Molecular Cloning. A Laboratory Manual*, 2d ed., Cold Spring Harbor Laboratory (1989)) to the sequences of SEQ ID NOS: 1 and 3, their anti-sense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g., hybridization in 4×SSC at 55° C., followed by washing in 0.1×SSC at 37° C. for an hour. An alternative exemplary moderately high stringency hybridization condition is in 50% formamide, 4×SSC at 30° C.

According to the invention, the nucleic acid sequences may be modified. Utilizing the sequence data of SEQ ID NOS: 1 and 3, it is within the skill of the art to obtain other synthetically or recombinantly-prepared polynucleotide sequences, or modified polynucleotide sequences, encoding the full-length proteins or useful fragments of the invention. For example, one of skill may employ preferred or "preference" codons for expression of the sequence in selected host cells; thus SEQ ID NOS: 1 and 3 may be modified to contain different nucleotide triplets which encode the same amino acid as encoded by SEQ ID NOS: 1 and 3. Such modifications made at the nucleic acid level include, for example, modifications to the nucleotide sequences which are silent or which change the amino acids, e.g. to improve expression or secretion of the protein. Also included are allelic variations, caused by the natural degeneracy of the genetic code.

Also encompassed by the present invention are mutants of the omp85 sequences, including 5', 3' or internal deletions, which encode proteins that substantially retain the antigenicity of the full-length Omp85 or other proteins or fragments. Such truncated, or deletion, mutants may be expressed by modified nucleic acid sequences for the purpose of affecting the activity of the full-length or wild-type protein.

As described in more detail below, these nucleic acid sequences are useful for a variety of diagnostic, prophylactic and therapeutic uses. Advantageously, the nucleic acid sequences are useful in the development of diagnostic probes and antisense probes for use in the detection and diagnosis of infections, particularly non-symptomatic infection, and diseases caused by these *Neisseriae* pathogens and by related pathogens discussed above by utilizing a variety of known nucleic acid assays, e.g., Northern and Southern blots, polymerase chain reaction (PCR), and other assay techniques known to one of skill in the art. The nucleic acid sequences of this invention are also useful in the production of Omp85 proteins and homologs as well as a variety of fusion or other synthetic proteins.

The nucleotide sequences of the invention may be readily synthesized or may be isolated by conventional uses of polymerase chain reaction or cloning techniques such as those described herein and in conventional texts such as Sambrook et al, cited above. For example, the nucleic acid sequences of the antigen of this invention may be prepared or isolated from genomic libraries using DNA primers and probes and PCR techniques. These sequences, fragments thereof, modifications thereto and the full-length sequences may be constructed recombinantly using conventional genetic engineering or chemical synthesis techniques or PCR, and the like by utilizing the information provided herein. Further, such nucleic acid sequences may be conventionally labeled for diagnostic use. Alternatively for use as therapeutic or vaccine components, the nucleic acid sequences of this invention may be admixed with a variety of pharmaceutically acceptable carriers, e.g., saline, liposomes, etc. or incorporated into nucleic acid molecules, e.g., plasmids under the regulatory control of sequences which direct expression of the encoded protein in a selected host cell. The nucleic acid sequences may also be delivered to a host as "naked" DNA or in a gene delivery vehicle, such as a recombinant virus, all as described in detail below.

B. Protein Sequences

The present invention also provides Omp85 proteins and peptides of this invention. These proteins are free from association with other contaminating proteins or materials with which they are found in nature. The *Neisseriae* Omp85 antigen has a relative molecular mass of 85 kDa as measured by Western immunoblot (See Example 2 and FIGS. 2A-2C). In one embodiment, the invention provides a gonococcal Omp85 antigen (SEQ ID NO:2) polypeptide of about 792 amino acids, with a signal peptide, having a predicted molecular weight of 85,842 daltons.

The meningococcal omp85 was found to encode a 797 amino acid polypeptide with a predicted molecular weight of 88.5 kDa (FIG. 5). Between amino acid residues 720 and 745, the menigococcal Omp85 varied substantially from gonococcal Omp85, including the insertion of five additional amino acids. The deduced amino acid sequence (SEQ ID NO: 4) of *N. meningitidis* Omp85 was revealed by sequence analysis to be 95% identical to *N. gonorrhoeae* Omp85 and 98% similar to gonococcal Omp85 using the BLAST2 algorithm.

The similarities of these two Omp85 proteins to proteins of other microorganisms provide evidence of an immunological role played by these proteins, as well as other potential roles. The D-15 protective surface antigen (D-15-Ag) of *Haemophilus influenzae* and the Oma87 of *Pasteurella multocida* are the only bacterial proteins, which have been previously described, that are similar to the Omp85 amino acid sequence (SEQ ID NO: 2). This similarity suggested that these proteins played an important role in host-pathogen interactions and have an important function in pathogenesis. The importance of these Omp85 proteins in pathogenesis and immunobiology was demonstrated by the fact that antibody to similar proteins in *H. influenzae* and *P. multocida* were protective. The similarities suggest that the *Neisseriae* Omp85 proteins are likely important immunological targets of the host immune response.

Western blot analysis demonstrated proteins similar to Omp85 in all of the *Neisseriae* tested with anti-Omp85 in three *Neisseriae* relationship areas. Area A contains the frank pathogens *N. gonorrhoeae* and *N. meningitidis* and opportunistic organisms known to cause severe human diseases such as *N. pharyngis* and *N. cinerea*. Area B contains species, such as *N. mucosae* and *N. lactamica*, typically found in the human nasopharynx which are able to cause opportunistic infections in debilitated hosts. Area C consists of commensal/saprophytic organisms, such as *N. flavescens, N. animalis* and *N. denitricans*, which generally do not cause human infections.

All *Neisseriae* species colonize mucosal surfaces. The presence of Omp85-like proteins in numerous pathogenic and commensal organisms suggests it may be involved in establishing or maintaining colonization. The identification of Omp85 proteins in a number of pathogenic and commensal organisms provides evidence that the Omp85 proteins provide functions involved in establishing or maintaining colonization.

Database searches identified genes in a number of pathogens which encode hypothetical proteins similar to Omp85, including genes in *B. abortus, H. pylori*, and *B. burgdorferi*. The proteins encoded by these genes have not yet been characterized. A search of the Omp85 amino acid sequence against the GenBank data base resulted in the identification of a cyanobacterium protein (Kaneto T. et al, *DNA Res.*, 3: 109-136 (1996)) with 35% similarity to the gonococcal Omp85. The cyanobacterium protein was named IAP75 because of its similarity to the 75 kDa chloroplast import associated protein, IAP75 (Schnell D J et al, *Science*, 266: 1007-1011 (1994)). The chloroplast IAP75 was located in the outer membrane of chloroplasts and was one of four outer membrane components of a complex that transports polypeptides. This suggested that Omp85 might be part of a similar transport complex.

The sequences of other proteins from the chloroplast import associated complex were searched against the Gonococcal Genome Sequencing Project Data Base (Dyer and Rowe, 1997). Sequences similar to the chloroplast IAP34 protein (Kessler F. et al, *Science*, 266: 1035-1039 (1994)) were identified in the gonococcal genome. IAP34 is believed to be a GTP-binding protein and the sequences of highest similarity to the gonococcal homolog were in regions identified as GTP-binding protein motifs. Surface-crosslinkage studies were performed to determine if Omp85 might participate in a system analogous to the IAP complex (data not shown). Studies using the reversible crosslinker DTBP, which crosslinks proteins that are within 11.9 Å of each other (Newhall W J. et al, *Infect. Immun.*, 28: 785-791 (1980)), showed that Omp85 crosslinked with up to five other outer membrane proteins, one of 34 kDa (IAP34 homolog) (data not shown). These data, which confirmed Omp85 was exposed on the bacterial surface, support the role for Omp85 of participating in a complex analogous to that of the chloroplast IAP complex. Further characterization of proteins associated with Omp85 in the outer membrane may provide evidence of additional biological functions of these Omp85 proteins.

One of skill in the art using conventional techniques, such as PCR, may readily use the Omp85 sequences provided herein to identify and isolate other similar proteins. Such methods are routine and not considered to require undue experimentation, given the information provided herein.

Antigens of this invention may be characterized by immunological measurements including, without limitation, Western blot, macromolecular mass determinations by biophysical determinations, such as SDS-PAGE/staining, high pressure liquid chromatography (HPLC) and the like, antibody recognition assays, T-cell recognition assays, major histocompatibility complex (MHC) binding assays, and assays to infer immune protection or immune pathology by adoptive transfer of cells, proteins or antibodies.

The Omp85 outer membrane antigens of this invention (as well as its naturally occurring variants or analogs in other species) may be isolated in the form of a complete intact protein, or a polypeptide or fragment thereof. In one embodiment, Omp85 is isolated by immunoblot procedures according to its respective molecular mass, as described below in the examples. Such isolation provides the antigen in a form substantially free from other proteinaceous and non-proteinaceous materials of the microorganism. The molecules comprising the polypeptides and antigens of this invention may be isolated and further purified using any of a variety of conventional methods including, but not limited to: liquid chromatography such as normal or reverse phase, using HPLC, FPLC and the like, affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Alternatively, the amino acid sequences of the proteins of this invention may be produced recombinantly following conventional genetic engineering techniques (see e.g., Sambrook et al, cited above and the detailed description of making the proteins below).

i. Analogs/Modified Antigens

Also included in the invention are analogs, or modified versions, of the Omp85 protein or fragments provided herein. Typically, such analogs differ from the specifically identified proteins by only one to four codon changes. Examples include polypeptides with minor amino acid variations from the illustrated partial amino acid sequence of, for example, the gonococcal Omp85 (SEQ ID NO: 2), in particular, conservative amino acid replacements. Conservative replacements are those that take place within a family of amino acids that are related in their side chains and chemical properties. Also provided are homologs of the proteins of the invention which are characterized by having at least 80% identity with SEQ ID NO:2 or SEQ ID NO: 4. Also included in this invention are homologs having at least 85% identity with SEQ ID NO: 2 or SEQ ID NO: 4. Homologs having at least 90% identity with either SEQ ID NO: 2 or SEQ ID NO: 4 are also encompassed by this invention. Homologs having at least 95% identity with either SEQ ID NO: 2 or SEQ ID NO: 4 are also encompassed by this invention. Also provided are homologs of the proteins of the invention which are characterized by having at least 85% homology with SEQ ID NO:2 or SEQ ID NO: 4. Also included in this invention are homologs having at least 90% homology with SEQ ID NO: 2 or SEQ ID NO: 4. Homologs having at least 95% homology with either SEQ ID NO: 2 or SEQ ID NO: 4 are also encompassed by this invention. Homologs having at least 99% homology with either SEQ ID NO: 2 or SEQ ID NO: 4 are also encompassed by this invention. The algorithms used for these calculations are identified above. Based on the sequence information provided herein, one of skill in the art can readily obtain full-length homologs and analogs from other bacterial species.

An antigen of the present invention may also be modified to increase its immunogenicity. For example, the antigen may be coupled to chemical compounds or immunogenic carriers, provided that the coupling does not interfere with the desired biological activity of either the antigen or the carrier. For a review of some general considerations in coupling strategies, see *Antibodies, A Laboratory Manual*, Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, purified protein derivative of tuberculin (PPD); red blood cells; tetanus toxoid; cholera toxoid; agarose beads; activated carbon; or bentonite. Useful chemical compounds for coupling include, without limitation, dinitrophenol groups and arsonilic acid. One of skill in the art may readily select other appropriate immunogenic carriers or coupling agents.

The antigen may also be modified by other techniques, such as denaturation with heat and/or SDS.

ii. Fragments/Deletion Mutants

Further encompassed by this invention are additional fragments of the Omp85 polypeptides and peptides identified herein. Such fragments are desirably characterized by having a biological activity similar to that displayed by the complete protein, including, e.g., the ability to induce antibodies which can interfere with the binding of the pathogen to its cellular targets (see Example 8). These fragments may be designed or obtained in any desired length, including as small as about 5-8 amino acids in length up to fragments encompassing just short of the entire protein. Such fragments may represent consecutive amino acids in the protein sequence or they may represent conformational sites of the protein. Such a fragment may represent an epitope or conformational epitope of the protein.

The Omp85 proteins (SEQ ID NOS:2 and 4) of the invention may be modified to create deletion mutants, for example, by truncation at the amino or carboxy termini, or by elimination of one or more amino acids. Deletion mutants are also encompassed by this invention, as are the DNA sequences encoding them.

In yet another embodiment, the Omp85 peptides or polypeptides of this invention may be in the form of a multiple antigenic peptide ("MAP", also referred to as an octameric lysine core peptide) construct. Such a construct may be designed employing the MAP system described by Tam, *Proc. Natl. Acad. Sci. USA*, 85:5409-5413 (1988). This system makes use of a core matrix of lysine residues onto which multiple copies of the same protein or peptide of the invention are synthesized as described (D. Posnett et al., *J. Biol. Chem.*, 263(4):1719-1725 (1988); J. Tam, "Chemically Defined Synthetic Immunogens and Vaccines by the Multiple Antigen Peptide Approach", *Vaccine Research and Developments*, Vol. 1, ed. W. Koff and H. Six, pp. 51-87 (Marcel Deblau, Inc., New York 1992)). Each MAP contains multiple copies of only one peptide.

Still other modified fragments of Omp85 may be prepared by any number of now conventional techniques to improve production thereof, to enhance protein stability or other characteristics, e.g. binding activity or bioavailability, or to confer some other desired property upon the protein. Other useful fragments of these polypeptides may be readily prepared by one of skill in the art using known techniques, such as deletion mutagenesis and expression.

iii. Fusion or Multimeric Proteins and Compositions

The Omp85 protein of the present invention, or fragments of it, may also be constructed, using conventional genetic engineering techniques as part of a larger and/or multimeric protein or protein compositions. Antigens of this invention may be in combination with outer surface proteins or other proteins or antigens of other pathogens, such as those identified above, or various fragments of the antigens described herein may be in combination with each other. In such combination, the antigen may be in the form of a fusion protein. The antigen of the invention may be optionally fused to a selected polypeptide or protein derived from other microorganisms. For example, an antigen or polypeptide of this invention may be fused at its N-terminus or C-terminus to a polypeptide from another pathogen or to more than one polypeptide in sequence. Polypeptides which may be useful for this purpose include polypeptides identified by the prior art.

Still another fusion protein of this invention is provided by expressing the DNA molecule formed by the omp85 DNA sequence or a fragment thereof fused to DNA fragments that are homologous (between about 25-95% identity) to Omp85. One example of such a protein comprises the amino acid sequence of SEQ ID NO: 2 to which is fused amino acid fragments that are up to 95% identical to that sequence, e.g., from SEQ ID NO: 4, or from any of the above-described homologous proteins. These fragments may be inserted in any order and may contain repeated sequences. The fused fragments may produce a large DNA molecule which expresses a protein which may stimulate a variety of antibody specificities.

These fusion proteins comprising multiple polypeptides of this invention are constructed for use in the methods and compositions of this invention. These fusion proteins or multimeric proteins may be produced recombinantly, or may be synthesized chemically. They also may include the polypeptides of this invention fused or coupled to moieties other than amino acids, including lipids and carbohydrates. Further, antigens of this invention may be employed in combination with other vaccinal agents described by the prior art, as well as with other species of vaccinal agents derived from other microorganisms. Such proteins are useful in the prevention, treatment and diagnosis of diseases caused by a wide spectrum of *Neisseriae* isolates.

A protein composition which may be a preferred alternative to the fusion proteins described above is a cocktail (i.e., a simple mixture) containing different Omp85 proteins or fragments, optionally mixed with different antigenic proteins or peptides of other pathogens. Such mixtures of these proteins or antigenic fragments thereof are likely to be useful in the generation of desired antibodies to a wide spectrum of *Neisseriae* isolates.

iv. Salts

An antigen of the present invention may also be used in the form of a pharmaceutically acceptable salt. Suitable acids and bases which are capable of forming salts with the polypeptides of the present invention are well known to those of skill in the art, and include inorganic and organic acids and bases.

III. Methods of Making Antigens and Nucleic Acid Sequences of the Invention

A. Expression In Vitro

To produce recombinant Omp85 or peptide fragments of this invention, the DNA sequences of the invention are inserted into a suitable expression system. Desirably, a recombinant molecule or vector is constructed in which the polynucleotide sequence encoding the selected protein, e.g., Omp85, is operably linked to a heterologous expression control sequence permitting expression of the protein. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, Sambrook et al, *Molecular Cloning. A Laboratory Manual*, 2d edition, Cold Spring Harbor Laboratory, New York (1989); Miller et al, *Genetic Engineering*, 8:277-298 (Plenum Press 1986) and references cited therein.

Suitable host cells or cell lines for transfection by this method include bacterial cells. For example, the various strains of *E. coli*, e.g., HB101, MC1061, and strains used in the following examples, are well-known as host cells in the field of biotechnology. Various strains of *B. subtilis, Pseudomonas, Streptomyces*, and other bacilli and the like are also employed in this method.

Mammalian cells, such as human 293 cells, Chinese hamster ovary cells (CHO), the monkey COS-1 cell line or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. (See, e.g., Gething and Sambrook, *Nature,* 293:620-625 (1981), or alternatively, Kaufman et al, *Mol. Cell. Biol.,* 5(7):1750-1759 (1985) or Howley et al, U.S. Pat. No. 4,419,446).

Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) cells may be used.

Thus, the present invention provides a method for producing recombinant Omp85 proteins, which involves transfecting, e.g., by conventional means such as electroporation, a host cell with at least one expression vector containing a polynucleotide of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art.

For example, the proteins are isolated in soluble form following cell lysis, or extracted using known techniques, e.g., in guanidine chloride. If desired, the proteins or fragments of the invention are produced as a fusion protein. Such fusion proteins are those described above. Alternatively, for example, it may be desirable to produce fusion proteins to enhance expression of the protein in a selected host cell, to improve purification, or for use in monitoring the presence of the desired protein, e.g., Omp85, in tissues, cells or cell extracts. Suitable fusion partners for the proteins of the invention are well known to those of skill in the art and include, among others, β-galactosidase, glutathione-S-transferase, poly-histidine and maltose binding protein.

B. Expression In Vivo

Alternatively, where it is desired that the Omp85 (whether full-length or a fragment) be expressed in vivo, e.g., to induce antibodies, or alternatively where the omp85 is to be employed as a DNA vaccine, an appropriate vector for delivery is readily selected by one of skill in the art. Exemplary vectors for in vivo gene delivery are readily available from a variety of academic and commercial sources, and include, e.g., adeno-associated virus (International patent application No. PCT/US91/03440), adenovirus vectors (M. Kay et al, *Proc. Natl. Acad. Sci. USA,* 91:2353 (1994); S. Ishibashi et al, *J. Clin. Invest.,* 92:883 (1993)), or other viral vectors, e.g., various poxviruses, vaccinia, etc. Methods for insertion of a desired gene, e.g., Omp85, and obtaining in vivo expression of the encoded protein, are well known to those of skill in the art.

IV. Antibodies of the Invention

The present invention also provides antibodies capable of recognizing and binding the isolated, or modified, or multimeric antigens of this invention, including antibodies derived from mixtures of such antigens or fragments thereof. Certain of the antibodies of this invention may be specific to the *N. gonorrhoeae* or *N. meningitidis* Omp85 proteins, by binding to epitopes on the proteins which differ from the former species to the latter species. For example, an antibody specific for *N. gonorrhoeae* may bind an epitope on SEQ ID NO: 2 which is not present in SEQ ID NO: 4, or vice versa. Thus, an *N. gonorrhoeae* Omp85-specific antibody is defined herein as an antibody that binds an Omp85 antigen of *N. gonorrhoeae* only. An N meningitidis Omp85-specific antibody is defined herein as an antibody that binds an Omp85 antigen of *N. meningitidis* only. Alternatively, certain antibodies to these proteins may bind an epitope present on both the *N. gonorrhoeae* and *N. meningitidis* Omp85 proteins. Still other antibodies of this invention may bind an epitope on *N. gonorrhoeae* and *N. meningitidis* Omp85, and the same epitope on the other homologous proteins in homologous or heterologous species of bacteria having homologous proteins (described in Part I, B above). All of these antibodies are encompassed by this invention.

These antibodies are useful in diagnosis of gonococcal and meningococcal infection (non-symptomatic) as well as symptomatic diseases, caused by *N. gonorrhoeae, N. meningitidis* or other *Neisseriae* species, and in therapeutic compositions for treating humans and/or animals that test positive for infection, or, prior to testing, exhibit symptoms of such diseases. The antibodies are useful in diagnosis alone or in combination with antibodies to other antigens of this invention, as well as antibodies to other known antigens from homologous or completely heterologous species of microorganism. These antibodies are also useful in passive vaccine compositions, which vaccines may also be polyvalent, by containing antibodies to antigens of other microorganisms as well as antibodies to the Omp85 proteins of this invention.

The antibodies of this invention are generated by conventional means utilizing the isolated, recombinant or modified antigens of this invention, or mixtures of such antigens or antigenic fragments. For example, polyclonal antibodies are generated by conventionally stimulating the immune system of a selected animal or human with the isolated antigen or mixture of antigenic proteins or peptides of this invention, allowing the immune system to produce natural antibodies thereto, and collecting these antibodies from the animal or human's blood or other biological fluid.

For example, an antibody according to the invention is produced by administering to a vertebrate host the antigen or antigenic composition of this invention, e.g., Omp85. Preferably a recombinant version of Omp85 (rOmp85) or an Omp85 MAP is used as an immunogen. A suitable polyclonal antibody against the Omp85 antigen may be generated as antisera, such as the Omp85 antisera employed in the examples herein.

Thus, an antibody of the invention is isolated by affinity purifying antiserum generated during an infection of a mammal, e.g., a mouse, with *N. gonorrhoeae* or *N. meningitidis,* using as immunoabsorbant the Omp85 antigen identified herein. Similarly, an antibody of the invention is isolated by immunizing mice with a purified, recombinant antigen of this invention, or a purified, isolated Omp85 protein of native origin.

Monoclonal antibodies (MAbs) directed against Omp85 are also generated. Hybridoma cell lines expressing desirable MAbs are generated by well-known conventional techniques, e.g. Kohler and Milstein and the many known modifications thereof. Similarly desirable high titer antibodies are generated by applying known recombinant techniques to the monoclonal or polyclonal antibodies developed to these antigens (see, e.g., PCT Patent Application No. PCT/GB85/00392; British Patent Application Publication No. GB2188638A; Amit et al., *Science,* 233:747-753 (1986); Queen et al., *Proc. Nat'l. Acad. Sci. USA,* 86:10029-10033 (1989); PCT Patent Application No. WO90/07861; and Riechmann et al., *Nature,* 332:323-327 (1988); Huse et al, *Science,* 246:1275-1281 (1988)a).

Given the disclosure contained herein, one of skill in the art may generate chimeric, humanized or fully human antibodies directed against Omp85 or antigenic fragments thereof by resort to known techniques by manipulating the complementarity determining regions of animal or human antibodies to the antigen of this invention. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994).

Alternatively, the antigens are assembled as multi-antigenic complexes (see, e.g., European Patent Application 0339695, published Nov. 2, 1989) or as simple mixtures of antigenic proteins/peptides and employed to elicit high titer antibodies capable of binding the selected antigen(s) as it appears in the biological fluids of an infected animal or human.

Further provided by the present invention are anti-idiotype antibodies (Ab2) and anti-anti-idiotype antibodies (Ab3). Ab2 are specific for the target to which anti-Omp85 antibodies of the invention bind and Ab3 are similar to Omp85 antibodies (Ab1) in their binding specificities and biological activities (see, e.g., M. Wettendorff et al., "Modulation of anti-tumor immunity by anti-idiotypic antibodies." in *Idiotypic Network and Diseases*, ed. by J. Cerny and J. Hiernaux J, Am. Soc. Microbiol., Washington D.C.: pp. 203-229, (1990)). These anti-idiotype and anti-anti-idiotype antibodies are produced using techniques well known to those of skill in the art. Such anti-idiotype antibodies (Ab2) can bear the internal image of Omp85 or fragments thereof and are thus useful for the same purposes as Omp85 or the fragments.

In general, polyclonal antisera, monoclonal antibodies and other antibodies which bind to the selected antigen (Ab1) are useful to identify epitopes of Omp85 to separate Omp85 and analogs thereof from contaminants in living tissue (e.g., in chromatographic columns and the like), and in general as research tools and as starting material essential for the development of other types of antibodies described above. Anti-idiotype antibodies (Ab2) are useful for binding the same target and thus may be used in place of the original antigen, e.g., Omp85, to induce an immune response. The Ab3 antibodies are useful for the same reason the Ab1 are useful. Other uses as research tools and as components for separation of Omp85 from other contaminants, for example, are also contemplated for the above-described antibodies.

For use in diagnostic assays, the antibodies are associated with conventional labels which are capable, alone or in concert with other compositions or compounds, of providing a detectable signal. Where more than one antibody is employed in a diagnostic method, the labels are desirably interactive to produce a detectable signal. Most desirably, the label is detectable visually, e.g. calorimetrically. A variety of enzyme systems have been described in the art which will operate to reveal a calorimetric signal in an assay. As one example, glucose oxidase (which uses glucose as a substrate) releases peroxide as a product. Peroxidase, which reacts with peroxide and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that may be utilized in the methods of this invention are detectable by other means, e.g., colored latex microparticles (Bangs Laboratories, Indiana) in which a dye is embedded may be used in place of enzymes to form conjugates with the antibodies and provide a visual signal indicative of the presence of the resulting complex in applicable assays. Stilt other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed.

V. Diagnostic Methods and Assays

The present invention also provides methods of diagnosing infections and diseases caused by infection with *N. gonorrhoeae, N. meningitidis* or possibly other species of pathogen which have homologous proteins to the Omp85 proteins of this invention. These diagnostic methods are useful for diagnosing humans having non-symptomatic infection or exhibiting the clinical symptoms of gonococcal or meningococcal disease, or possibly any of the other diseases caused by homologous bacterial species.

In one embodiment, this diagnostic method involves detecting the presence of naturally occurring anti-Omp85 antibodies which are produced by the infected human or animal patient's immune system in its biological fluids, and which are capable of binding to the antigens of this invention or combinations thereof. This method comprises the steps of incubating a Omp85 antigen or antigenic fragment of this invention with a sample of biological fluid or tissue from the patient. Antibodies present in the fluids as a result of bacterial infection will form an antibody-antigen complex with the antigen. Subsequently the reaction mixture is analyzed to determine the presence or absence of these antigen-antibody complexes. The step of analyzing the reaction mixture can comprise detecting a label associated with the Omp85 antigen, or contacting the reaction mixture with a labeled specific binding partner for the antibody or antibody.

In one embodiment of the method, purified antigen, fragment or mixture of antigens is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody is then detected by standard immunoenzymatic methods.

In another embodiment of the method, latex beads are conjugated to the antigen(s) of this invention. Subsequently, the biological fluid is incubated with the bead/protein conjugate, thereby forming a reaction mixture. The reaction mixture is then analyzed to determine the presence of the antibodies.

In another embodiment, the diagnostic method of the invention involves detecting the presence of the naturally occurring Omp85 itself in its association with the *Neisseriae* pathogen in the biological fluids or tissue of an animal or human infected by the pathogen. This method includes the steps of incubating an antibody of this invention (e.g. produced by administering to a suitable human and/or animal an antigen of this invention preferably conventionally labeled for detection) with a biological sample from a human or an animal to be diagnosed. In the presence of infection of the human or animal patient, an antigen-antibody complex is formed (specific binding occurs). Subsequently, excess labeled antibody is optionally removed, and the reaction mixture is analyzed to determine the presence or absence of the antigen-antibody complex and the amount of label associated therewith.

Assays employing a protein antigen of the invention can be heterogenous (i.e., requiring a separation step) or homogenous. If the assay is heterogenous, a variety of separation means can be employed, including centrifugation, filtration, chromatography, or magnetism.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-*N. gonorrhoeae* or *N. meningitidis* antibody. The sample can be applied neat, or more often, it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with labeled anti-human immunoglobulin ($\alpha$ HuIg) or labeled antibodies to other species, e.g., dogs. The label can be chosen from a variety of enzymes, including horseradish peroxidase (HRP), $\beta$-galactosidase, alkaline phosphatase, and glucose oxidase, as described above. Sufficient time is allowed for specific binding to occur again, then the well is washed again to remove unbound conjugate, and the substrate for the enzyme is added. Color is allowed to develop and the optical density of the contents of the well is determined visually or instrumentally.

Further, MAbs or other antibodies of this invention which are capable of binding to the antigen(s) can be bound to ELISA plates. In another diagnostic method, the biological fluid is incubated on the antibody-bound plate and washed. Detection of any antigen-antibody complex, and qualitative measurement of the labeled MAb are performed conventionally, as described above.

Other useful assay formats include the filter cup and dipstick. In the former assay, an antibody of this invention is fixed to a sintered glass filter to the opening of a small cap. The biological fluid or sample (5 ml) is worked through the filter. If the antigen is present (i.e., *N. gonorrhoeae* infection), it will bind to the filter which is then visualized through a second antibody/detector. The dipstick assay involves fixing an antigen or antibody to a filter, which is then dipped in the biological fluid, dried and screened with a detector molecule.

Other diagnostic assays can employ the omp85 gene sequences or fragments of this invention as nucleic acid probes or an anti-sense sequences, which can identify the presence of infection in the biological fluid by hybridizing to complementary sequences produced by the pathogen in the biological fluids. Such techniques, such as PCR, Northern or Southern hybridizations etc. are well known in the art. For this purpose, the nucleic acid sequences or fragments of this invention may be conventionally labelled by well known techniques, possibly employing one or more of the labels described above with reference to use of the antibodies, or with labels more suited for attachment to nucleic acids. Selection of such labels is a routine matter and does not limit this invention.

It should be understood by one of skill in the art that any number of conventional protein assay formats, particularly immunoassay formats, or nucleic acid assay formats, may be designed to utilize the isolated antigens and antibodies or their nucleic acid sequences or anti-sense sequences of this invention for the detection of *N. gonorrhoeae* or *N. meningitidis* infection (as well as infection with other bacteria characterized by antigens homologous to the Omp85 antigens of this invention) in animals and humans. This invention is thus not limited by the selection of the particular assay format, and is believed to encompass assay formats which are known to those of skill in the art.

VI. Diagnostic Kits

For convenience, reagents for ELISA or other assays according to this invention may be provided in the form of kits. Such kits are useful for diagnosing bacterial infection in a human or an animal sample. Such a diagnostic kit contains an antigen of this invention and/or at least one antibody capable of binding an antigen of this invention, or the nucleic acid sequences encoding such Omp85 antigens or antibodies or their anti-sense sequences. Alternatively, such kits may contain a simple mixture of such antigens or nucleic acid sequences, or means for preparing a simple mixture.

These kits can include microtiter plates to which the antigenic proteins or antibodies or nucleic acid sequences of the invention have been pre-adsorbed, various diluents and buffers, labeled conjugates for the detection of specifically bound antigens or antibodies, or nucleic acids and other signal-generating reagents, such as enzyme substrates, cofactors and chromogens. Other components of these kits can easily be determined by one of skill in the art. Such components may include polyclonal or monoclonal capture antibodies, antigen of this invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for calorimetric comparisons, disposable gloves, decontamination instructions, applicator sticks or containers, and a sample preparator cup. Such kits provide a convenient, efficient way for a clinical laboratory to diagnose *N. gonorrhoeae* or *N. meningiditus* infection.

VII. Therapeutic and Vaccine Compositions

A. Protein-Containing Therapeutic and Vaccine Compositions

The antigens and antibodies of the invention, alone or in combination with other antigens and antibodies of, or directed to, other pathogenic microorganisms may further be used in therapeutic compositions and in methods for treating humans and/or animals with non-symptomatic infection or symptomatic disease caused by *N. gonorrhoeae, N. meningitidis* or the other pathogens identified above.

For example, one such therapeutic composition may be formulated to contain a carrier or diluent and one or more of the anti-Omp85 antibodies of the invention. In compositions containing the Omp85 antigen or antibodies thereto, i.e., protein components, suitable pharmaceutically acceptable carriers may be employed that facilitate administration of the proteins but are physiologically inert and/or nonharmful.

A variety of such pharmaceutically acceptable protein carriers, and/or components suitable for administration therewith may be selected by one of skill in the art. For example, pharmaceutical carriers include, without limitation, sterile saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used. Liposomes or liposomal-like vehicles may also be employed.

Optionally, these compositions may also contain conventional pharmaceutical ingredients, such as preservatives, or chemical stabilizers. Suitable ingredients which may be used in a therapeutic composition in conjunction with the antibodies include, for example, casamino acids, sucrose, gelatin, phenol red, N-Z amine, monopotassium diphosphate, lactose, lactalbumin hydrolysate, and dried milk.

Alternatively, or in addition to the antigens or antibodies of the invention, other agents useful in treating the disease in question, e.g., antibiotics or immunostimulatory agents and cytokine regulation elements, are expected to be useful in reducing or eliminating disease symptoms. Such agents may operate in concert with the therapeutic compositions of this invention. The development of therapeutic compositions containing these agents is within the skill of one in the art in view of the teachings of this invention.

Additionally, the therapeutic compositions may be polyvalent. Such compositions may contain therapeutic components from other bacterial or viral pathogens, e.g., components of bacterial species homologous to *Neiserriae* or heterologous thereto and/or antigens from a disease-causing virus. Depending upon the compatibility of the components, the Omp85 antibodies or antigens of this invention may thus be part of a multi-component therapeutic composition directed at more than a single disease.

As a further embodiment of this invention, a therapeutic method involves treating a human or an animal for infection with *N. gonorrhoeae* or *N. meningitidis* by administering an effective amount of such a therapeutic composition. An "effective amount" of a proteinaceous composition may be between about 0.05 to about 1000 µg/ml of an antibody or antigen of the invention. A suitable dosage may be about 1.0 ml of such an effective amount. Such a composition may be administered 1-3 times per day over a 1 day to 12 week period. However, suitable dosage adjustments for protein or nucleic acid containing compositions may be made by the attending physician or veterinarian depending upon the age, sex, weight and general health of the human or animal patient. Preferably, such a composition is administered parenterally, preferably intramuscularly or subcutaneously. However, it may also be formulated to be administered by any other suitable route, including orally or topically. The selection of the route of delivery and dosage of such therapeutic compositions is within the skill of the art.

In another embodiment, the Omp85 antigens, antibodies, and fragments of the invention, alone or in combination with other antigens, antibodies, and fragments from other microorganisms, may further be used in compositions directed to induce a protective immune response in a subject to the pathogen. These components of the present invention are also useful in methods for inducing a protective immune response in humans and/or animals against infection with *N. gonorrhoeae, N. meningitidis* or the other pathogens identified above.

In one embodiment, an outer membrane protein antigen-based vaccine for the prevention of non-symptomatic gonococcal infection or symptomatic disease, non-symptomatic meningococcal infection and symptomatic disease, and other diseases in humans and other animals is provided which contains an effective amount of the Omp85 antigen of this invention, and a pharmaceutically acceptable carrier or diluent. This vaccine composition may contain one or more of the isolated, recombinant, modified or multimeric forms of the Omp85 antigen of the invention, or mixtures thereof. Similarly, salts of the antigenic proteins may be employed in such compositions.

In another embodiment of this invention, a polyvalent vaccine composition may include not only the Omp85 antigen or immunogenic fragment thereof, but may also include antigens from other disease-causing agents. Such other agents may be antigens from other *Neisseriae* strains. Such other agents may be antigens from completely distinct bacterial pathogens or from viral pathogens. Combinations of the antigen(s) of this invention with other antigens or fragments thereof are also encompassed by this invention for the purpose of inducing a protective immune response in the vaccinated subject to more than a single pathogen. The selection of these other vaccine components is not a limitation of the present invention, and may be left to one of skill in the art.

Such proteinaceous vaccines may include exemplary carriers as described above for therapeutic compositions. Optionally, the vaccine compositions may optionally contain adjuvants, preservatives, chemical stabilizers, as well as other conventionally employed vaccine additives. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol.

With regard to the adjuvant, one or more of the above described vaccine components may be admixed or adsorbed with a conventional adjuvant. The adjuvant is used to attract leukocytes or enhance an immune response. Such adjuvants include, among others, RIBI adjuvant, mineral oil and water, aluminum hydroxide, AMPHIGEN adjuvant, ADJUVAX adjuvant, AVRIDINE adjuvant, L121/squalene, D-lactide-polylactide/glycoside, pluronic plyois, muramyl dipeptide, killed *Bordetella*, and saponins, such as Quil A.

The invention thus also encompasses a prophylactic method entailing administering to an animal or human an effective amount of such a composition. The protein antigenic composition is administered in an "effective amount", that is, an amount of antigen that is effective in a route of administration to provide a vaccinal benefit, i.e., protective immunity. Suitable amounts of the antigen can be determined by one of skill in the art based upon the level of immune response desired. In general, however, the vaccine composition contains between 1 ng to 1000 mg antigen, and more preferably, 0.05 µg to 1 mg per ml of antigen. Suitable doses of the vaccine composition of the invention can be readily determined by one of skill in the art. Generally, a suitable dose is between 0.1 to 5 ml of the vaccine composition. Further, depending upon the human patient or the animal species being treated, i.e. its weight, age, and general health, the dosage can also be determined readily by one of skill in the art.

In general, the vaccine can be administered once; and optionally boosters can be administered periodically thereafter. The vaccine may be administered by any suitable route. However, parenteral administration, particularly intramuscular, and subcutaneous, is the preferred route. Also preferred is the oral route of administration. Routes of administration may be combined, if desired, or adjusted.

In still another vaccine embodiment, the invention includes a composition which delivers passive protection against infection by the pathogen. For this composition, the antibodies against the Omp85 proteins disclosed herein are useful to provide to the subject a short-term, passive immune protection against infection. These passive immunity vaccine compositions may contain antibodies to other pathogens and suitable vaccine additives as described above, e.g., adjuvants, etc. These compositions may be administered in dosages similar to those described above for the compositions which actively induce immune protection in the vaccinated subject.

B. Nucleic Acid Containing Compositions The nucleic acid sequences or anti-sense sequences of the invention, alone or in combination with other nucleic acid sequences encoding antigens or antibodies of, or directed to other pathogenic microorganisms may further be used in therapeutic compositions and in methods for treating humans and/or animals with the disease caused by infection with *N. gonorrhoeae, N. meningitidis* or the other pathogens identified above. In another embodiment, the nucleic acid sequences of this invention, alone or in combination with nucleic acid sequences encoding other antigens or antibodies from other pathogenic microorganisms, may further be used in compositions directed to actively induce a protective immune response in a subject to the pathogen. These components of the present invention are useful in methods for inducing a protective immune response in humans and/or animals against infection with *N. gonorrhoeae, N. meningitidis* or the other pathogens identified above.

For use in the preparation of the therapeutic or vaccine compositions, nucleic acid delivery compositions and methods are useful, which are known to those of skill in the art. The omp85 sequences or fragments thereof (or anti-sense sequences as desired) may be employed in the methods of this invention or in the compositions described herein as DNA sequences, either administered as naked DNA, or associated with a pharmaceutically acceptable carrier. These sequences provide for in vivo expression of the Omp85 protein or peptide or provide for production of anti-sense sequences which can bind to the Omp85 protein in the subject due to infection. So-called 'naked DNA' may be used to express the Omp85 protein or peptide fragment (or anti-sense sequences) in vivo in a patient. See, e.g., J. Cohen, *Science,* 259:1691-1692 (Mar. 19, 1993); E. Fynan et al., *Proc. Natl. Acad. Sci., USA,* 90: 11478-11482 (December 1993); J. A. Wolff et al., *Biotechniques,* 11:474-485 (1991) which describe similar uses of 'naked DNA', all incorporated by reference herein. For example, "naked" omp85 DNA (or anti-sense sequences) associated with regulatory sequences may be administered therapeutically or as part of the vaccine composition e.g., by injection.

Alternatively, omp85 DNA or anti-sense DNA may be administered as part of a vector or as a cassette containing the Omp85-encoding DNA sequences or fragments or anti-sense sequences thereof operatively linked to a promoter sequence and other plasmid sequences. Briefly, the DNA encoding the Omp85 protein (or anti-sense sequence) or desired fragment thereof may be inserted into a nucleic acid cassette. This cassette may be engineered to contain, in addition to the omp85 sequence to be expressed (or anti-sense sequence), other optional flanking sequences which enable its insertion into a vector. This cassette may then be inserted into an appropriate DNA vector downstream of a promoter, an mRNA leader sequence, an initiation site and other regulatory sequences capable of directing the replication and expression of that sequence in vivo. This vector permits infection of vaccinate's cells and expression of the omp85 (or anti-sense sequence) in vivo.

Numerous types of appropriate vectors are known in the art for protein expression and may be designed by standard molecular biology techniques. Such vectors are selected from among conventional vector types including insects, e.g., baculovirus expression, or yeast, fungal, bacterial or viral expression systems. Methods for obtaining such vectors are well-known. See, Sambrook et al., *Molecular Cloning, A Laboratory Manual,* 2d edition, Cold Spring Harbor Laboratory, New York (1989); Miller et al., *Genetic Engineering,* 8:277-298 (Plenum Press 1986) and references cited therein. Recombinant viral vectors, such as retroviruses or adenoviruses, are preferred for integrating the exogenous DNA into the chromosome of the cell.

Also where desired, the regulatory sequences in such a vector which control and direct expression of the omp85 gene product or anti-sense sequence in the transfected cell include an inducible promoter. Inducible promoters are those which "turn on" expression of the gene when in the presence of an inducing agent. Examples of suitable inducible promoters include, without limitation, the sheep metallothionine (MT) promoter, the mouse mammary tumor virus (MMTV), the tet promoter, etc. The inducing agents may be a glucocorticoid such as dexamethasone, for, e.g., the MMTV promoter, or a metal, e.g., zinc, for the MT promoter; or an antibiotic, such as tetracycline for tet promoter. Still other inducible promoters may be selected by one of skill in the art, such as those identified in International patent application WO95/13392, published May 18, 1995, and incorporated by reference herein. The identity of the inducible promoter is not a limitation of this invention.

When omp85 nucleic acid sequences or anti-sense sequences are employed as the therapeutic agent or vaccine agent as 'naked DNA' operatively linked to a selected promoter sequence, rather than the protein itself, the amounts of DNA to be delivered and the routes of delivery may parallel the protein amounts for vaccine or therapeutic delivery described above and may also be determined readily by one of skill in the art.

Thus, as one preferred example, a therapeutic composition may be formulated to contain a carrier or diluent and one or more plasmid or DNA molecule or recombinant virus containing a nucleic acid sequence which is anti-sense to the omp85 gene sequence (SEQ ID NO: 1 or 3), a fragment thereof, under control of suitable sequences regulating the expression thereof. In compositions containing the anti-sense omp85 nucleic acid sequences, vehicles suitable for delivery of DNA may be employed.

Additionally, these therapeutic compositions may be polyvalent. Such compositions may contain therapeutic components which are anti-sense sequences of other bacterial or viral origin, e.g., the anti-sense sequence of components of bacterial species homologous to *Neiserriae* or heterologous thereto and/or anti-sense sequence derived from antigens from a disease-causing virus. Depending upon the compatibility of the components, the anti-sense sequences to the Omp85 antigens of this invention may thus be part of a multi-component therapeutic composition directed at more than a single disease.

As a further embodiment of this invention, a therapeutic method involves treating a human or an animal for infection with *N. gonorrhoeae* or *N. meningitidis* by administering an effective amount of such a therapeutic nucleic-acid containing composition. An "effective amount" of a nucleic acid composition may be calculated as that amount capable of expressing in vivo the above effective amounts of exogenously delivered proteins. Such amounts may be determined by one of skill in the art. Preferably, such a composition is administered parenterally, preferably intramuscularly or subcutaneously. However, it may also be formulated to be administered by any other suitable route, including orally or topically. The selection of the route of delivery and dosage of such therapeutic compositions is within the skill of the art.

As another example, a vaccine composition of this invention may be a DNA vaccine, which includes the omp85 DNA sequence (SEQ ID NOS: 1 or 3) or a fragment thereof which encodes an immunogenic protein or peptide, optionally under the control of regulatory sequences. In one embodiment, this vaccine composition may contain a nucleic acid sequence that encodes one or more of the isolated, recombinant, modified or multimeric forms of the Omp85 antigen of the invention, or mixtures thereof.

In another embodiment of this invention, polyvalent vaccine compositions may include not only the nucleic acid sequence encoding the Omp85 antigen or an immunogenic fragment thereof, but may also include nucleic acid sequences encoding antigens from other disease-causing agents. Such other agents may be antigens from other *Neisseriae* strains. Such other agents may be nucleic acid sequences encoding antigens from completely distinct bacterial pathogens or from viral pathogens. Combinations of the antigen-encoding sequences of this invention with other nucleic acid sequences encoding antigens or fragments thereof from other pathogens are also encompassed by this invention for the purpose of inducing a protective immune response in the vaccinated subject to more than a single pathogen. The selection of these other vaccine components is not a limitation of the present invention, and may be left to one of skill in the art.

Such "DNA" or nucleic acid vaccines may include exemplary carriers as described above for therapeutic compositions and, where suitable, the components or additives described above with reference to the proteinaceous compositions, e.g. adjuvants, preservatives, chemical stabilizers, etc. as well as other conventionally employed vaccine additives. Additives suitable for use in nucleic acid compositions are known to those of skill in the art, including certain lipids and liposomes, among other known components.

Generally, a suitable nucleic acid-based treatment contains between $1 \times 10^{-3}$ plaque forming unit (pfu) to $1 \times 10^{12}$ pfu per dose, if a virus is the delivery vector. Otherwise, the dosage is adjusted to provide the same amount of expressed protein as is provided by the protein vaccines. However, the dose, timing and mode of administration of these compositions may be determined by one of skill in the art. Such factors as the age, and physical condition of the vaccinate may be taken into account in determining the dose, timing and mode of administration of the immunogenic or vaccine composition of the invention.

VIII. Drug Screening and Development

The proteins, antibodies and polynucleotide sequences of the present invention may also be used in the screening and development of chemical compounds or proteins which have utility as therapeutic drugs or vaccines for the treatment or diagnosis or prevention of diseases caused by infection with *N. gonorrhoeae* or *N. meningitidis*, and possibly for the other microorganisms having homologous proteins to Omp85. As one example, a compound capable of binding to Omp85 and preventing its biological activity may be a useful drug component for the treatment or prevention of such non-symptomatic gonococcal infection or symptomatic diseases as gonorrhea and non-symptomatic meningococcal infection and symptomatic disease, e.g., spinal meningitis, among others. The methods described herein may also be applied to fragments of Omp85.

Suitable assay methods may be readily determined by one of skill in the art. Where desired, and depending on the assay selected, the selected antigen(s), e.g., Omp85 or fragment thereof, may be immobilized directly or indirectly (e.g., via an Omp85 antibody) on a suitable surface, e.g., in an ELISA format. Such immobilization surfaces are well known. For example, a wettable inert bead may be used. Alternatively, the selected antigen, e.g., Omp85, may be used in screening assays which do not require immobilization, e.g., in the screening of combinatorial libraries. Assays and techniques exist for the screening and development of drugs capable of binding to an antigen of this invention, e.g., Omp85. These include the use of phage display system for expressing the antigenic protein(s), and using a culture of transfected *E. coli* or other microorganism to produce the proteins for binding studies of potential binding compounds. See, for example, the techniques described in G. Cesarini, *FEBS Letters,* 307(1): 66-70 (July 1992); H. Gram et al., *J. Immunol. Meth.,* 161: 169-176 (1993); C. Summer et al., *Proc. Natl. Acad. Sci., USA,* 89:3756-3760 (May 1992), incorporated by reference herein.

Other conventional drug screening techniques may be employed using the proteins, antibodies or polynucleotide sequences of this invention. As one example, a method for identifying compounds which specifically bind to a protein of this invention, e.g., Omp85, can include simply the steps of contacting a selected Omp85 protein with a test compound to permit binding of the test compound to Omp85; and determining the amount of test compound, if any, which is bound to the Omp85 protein. Such a method may involve the incubation of the test compound and the Omp85 protein immobilized on a solid support. Similar methods may be employed for one or more of the cassette string proteins.

Typically, the surface containing the immobilized ligand is permitted to come into contact with a solution containing the protein and binding is measured using an appropriate detection system. Suitable detection systems include the streptavidin horse radish peroxidase conjugate, direct conjugation by a tag, e.g., fluorescein. Other systems are well known to those of skill in the art. This invention is not limited by the detection system used.

Another method of identifying compounds which specifically bind to Omp85 or another protein of this invention can include the steps of contacting the protein, e.g., Omp85, immobilized on a solid support with both a test compound and the protein sequence which is a receptor for Omp85 to permit binding of the receptor to the Omp85 protein; and determining the amount of the receptor which is bound to the Omp85 protein. The inhibition of binding of the normal protein by the test compound thereby indicates binding of the test compound to the Omp85 protein.

Still other conventional methods of drug screening can involve employing a suitable computer program to determine compounds having similar or complementary chemical structures to that of the Omp85 proteins (SEQ ID NOS: 2 and 4), and screening those compounds for competitive binding to Omp85. Such programs include the GRID program available from Oxford University, Oxford, UK. (P. J. Goodford, "A Computational Procedure for Determining Energetically Favorable Binding Sites on Biologically Important Macromolecules", *J. Med. Chem.,* 28:849-857 (1985)); the MCSS program available from Molecular Simulations, Burlington, Mass. (A. Miranker and M. Karplus, "Functionality Maps of Binding Sites: A Multiple Copy Simultaneous Search Method", *Proteins: Structure, Function and Genetics,* 11:29-34 (1991)); the AUTODOCK program available from Scripps Research Institute, La Jolla, Calif. (D. S. Goodsell and A. J. Olsen, "Automated Docking of Substrates to Proteins by Simulated Annealing", *Proteins: Structure, Function, and Genetics,* 8:195-202 (1990)); and the DOCK program available from University of California, San Francisco, Calif. (I. D. Kuntz et al., "A Geometric Approach to Macromolecule-Ligand Interactions", *J. Mol. Biol.,* 161:269-288 (1982)). Additional commercially available computer databases for small molecular compounds include Cambridge Structural Database, Fine Chemical Database, and CONCORD database. For a review see Rusinko, A., *Chem. Des. Auto. News,* 8:44-47 (1993).

Thus, the invention provides a method of identifying a pharmacomimetic of Omp85 of *N. gonorrhoeae* or *N. meningitidis* by using a combination of steps including identifying a compound which binds to Omp85 by screening said Omp85 against a battery of compounds. Computer modelling of the three dimensional structure of Omp85 or of the previously identified binding compound permits the identification of a compound with the same three dimensional structure as either Omp85 or its binding compound. The compound selected from these tests is then screened for the biological activity of Omp85 or of a compound that binds Omp85, such as the development of antisera effective in the assay of Example 8 or competitive effect in that assay, respectively.

Thus, through use of such methods, the present invention is anticipated to provide compounds capable of interacting with Omp85 or portions thereof, and either enhancing or decreasing its biological activity, as desired. Such compounds are believed to be encompassed by this invention.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Bacterial Strains, Cells, Methods and Culture Conditions

*N. gonorrhoeae* strains FA19, FA635, FA1090, JS1, F62 and MS11 LosA used in the examples below were provided by Dr. William M. Shafer (Emory University, Atlanta, Ga.) Dr. John Swanson (Rocky Mountain Laboratories, Hamilton, Mont.) or the American Type Culture Collection 10801 University Boulevard, Manassas, Va. 20110-2209. *N. meningitidis* strains MP78, MP3, MP81, and HH were provided by Dr. Mark S. Peppler (University of Alberta, Edmonton, Alberta, Canada) and Dr. Zell McGee (University of Utah, Salt Lake City, Utah). All other strains were acquired from the American Type Culture Collection. *Moraxella catarrhalis* (ATCC#8193) and *Neisserial* strains were grown on clear gonococcal typing media (Swanson J., *Infect. Immun.,* 19: 320-331 (1978)). *E. coli* and all other Gram negative strains were grown an Luria broth.

*E. coli* XL1-Blue and SOLR cells were obtained from Stratagene Cloning Systems (La Jolla, Calif.). DNA fragments were purified from agarose gels using GENE CLEAN™ II (Bio101, La Jolla, Calif.). Plasmids were purified using the QIAPREP™ quick spin kit (Qiagen, Chatsworth, Calif.). Immunoblotting was done with MILLIPORE IMMOBILON™ PVDF reagent (Bedford, Mass.). Unless specified otherwise in the examples below, all reagents were obtained from Sigma Chemical Co. (St. Louis, Mo.).

EXAMPLE 2

Cloning and Immunological Screening of A Gonococcal Genomic Library

A genomic DNA library was produced by purifying *N. gonorrhoeae* strain FA19 genomic DNA and partially digesting the DNA into fragments with the restriction endonuclease Tsp509 (New England Biolabs). These DNA fragments were ligated with T4 DNA ligase (New England Biolabs) into the EcoRI restriction site of the lambda ZAP II™ bacteriophage vector (Stratagene Cloning Systems, La Jolla, Calif.). The ligated phage DNA was packaged, and plated on *E. coli* DH5α (Gibco BRL, Gaithersburg, Md.) host cells. The resulting library was screened immunologically for the expression of gonococcal surface proteins according to protocols provided with the Lambda ZAP II™ vector system. The plaques from the library were screened with anti-GC-OM, an antiserum raised to isolated gonococcal outer membranes.

Plasmid DNA was rescued from phage producing immunoreactive plaques. The plasmid, pDR4, contained a 2.6 kbp gonococcal DNA insert. The gonococcal DNA in pDR4 was subcloned into pUP1 (Elkins C., *J. Bacteriol.,* 173: 3911-3913 (1991), generously provided by Dr. Chris Elkins (University of North Carolina, Chapel Hill, N.C.) yielding pOmp85.

The cloned gonococcal DNA fragment in pOmp85 was characterized by restriction enzyme analysis. The fragment contained three internal HincII restriction sites which allowed the subcloning of three fragments into PBluescript™ plasmid (Stratagene Cloning Systems, La Jolla, Calif.). These fragments and pDR4 were sequenced by the University of Montana Molecular Biology Facility. A gene-walking strategy was used to sequence those regions which could not be sequenced with universal vector primers. The entire length of the gonococcal DNA fragment was sequenced at least twice and most of the DNA was sequenced from both strands. The deduced amino acid sequence and comparisons of Omp85 homologs were obtained with the MACVECTOR™ software package (Eastman Chemical Co., New Haven, Conn.).

The 2.6 kb gonococcal DNA in pOmp85 was found to contain a large open reading frame (ORF) which encoded a polypeptide of 792 amino acids with a predicted molecular weight of 87.8 kDa (FIGS. 2A-2C) (SEQ ID NO:2). The polypeptide contained a putative signal peptide (Von Heijne G., *Nuc. Acids Res.,* 14: 4683-4690 (1986)). Removal of this signal peptide yielded a mature polypeptide with an 85.8 kDa predicted molecular weight. The polypeptide also possesses a carboxyl-terminal phenylalanine residue characteristic of outer membrane proteins (Struyve M. et al., *J. Mol. Biol.,* 218: 141-148 (1991)). A ribosome-binding sequence preceded the initiation codon of the ORF. Potential promoter sequences were not readily apparent. The ORF was preceded and followed by putative rho-independent transcriptional stop sites. The approximately 85 kDa gonococcal protein expressed by pOmp85 was designated Omp85 and the gene encoding it was designated omp85.

EXAMPLE 3

Cloning and Sequencing of Meningococcal omp85

The meningococcal omp85 was obtained by PCR amplification using the Boehringer Mannheim EXPAND HIGH FIDELITY™ PCR System (Indianapolis, Ind.). The design of PCR primers was based on gonococcal omp85 and flanking sequences. The positive-sense omp85 PCR primer contained the first five codons of the gonococcal omp85 with an EcoRI restriction site and two extra nucleotides added to the 5' end (CGGAATTCATGAAACTGAAACAG) (SEQ ID NO: 5). The negative-sense omp85 PCR primer contained the reverse-compliment of six codons (TTGCAGTTTTTG-CAATTC) (SEQ ID NO: 6) of the gonococcal ompH sequence located 244 base pairs 3' of omp85 termination codon. These primers were used in a PCR reaction with purified *N. meningitidis* HH DNA as template. The meningococcal omp85 PCR product was ligated into pUP1 to yield pMCOmp85. The sequence of the meningococcal omp85 was obtained essentially as described for the gonococcal omp85.

The meningococcal omp85 was found to encode a 797 amino acid polypeptide with a predicted molecular weight of 88.5 kDa (FIG. 5). The meningococcal Omp85 was 95% identical and 98% similar to gonococcal Omp85. Between amino acid residues 720 and 745, the menigococcal Omp85 varied substantially from gonococcal Omp85, including the insertion of five additional amino acids.

EXAMPLE 4

Presence of omp85 in Strains of *N. Gonorrhoeae* and *N. Meningitidis*

A. Western Analysis

The Western blot analyses were performed as follows. Bacterial proteins were separated by SDS-PAGE (12.5%) (Laemmli UK, *Nature*, 227: 680-695 (1970)). The separated proteins were electrophoretically transferred onto PVDF as previously described (Judd R C., *Anal. Biochem.*, 173: 307-316 (1988)). Blotting was performed in 20 mM sodium phosphate buffer, pH 8.0 for 2 hr at 600 mA. The PVDF membrane was blocked for 1 hr with PBS Tween at room temperature, incubated overnight in anti-GC-OM or anti-Omp85 sera at 4° C., washed several times, incubated with protein A-horseradish peroxidase conjugate (Boehringer Mannheim, Indianapolis, Ind.) and developed with 4-chloro-1-naphthol.

Figure 1:
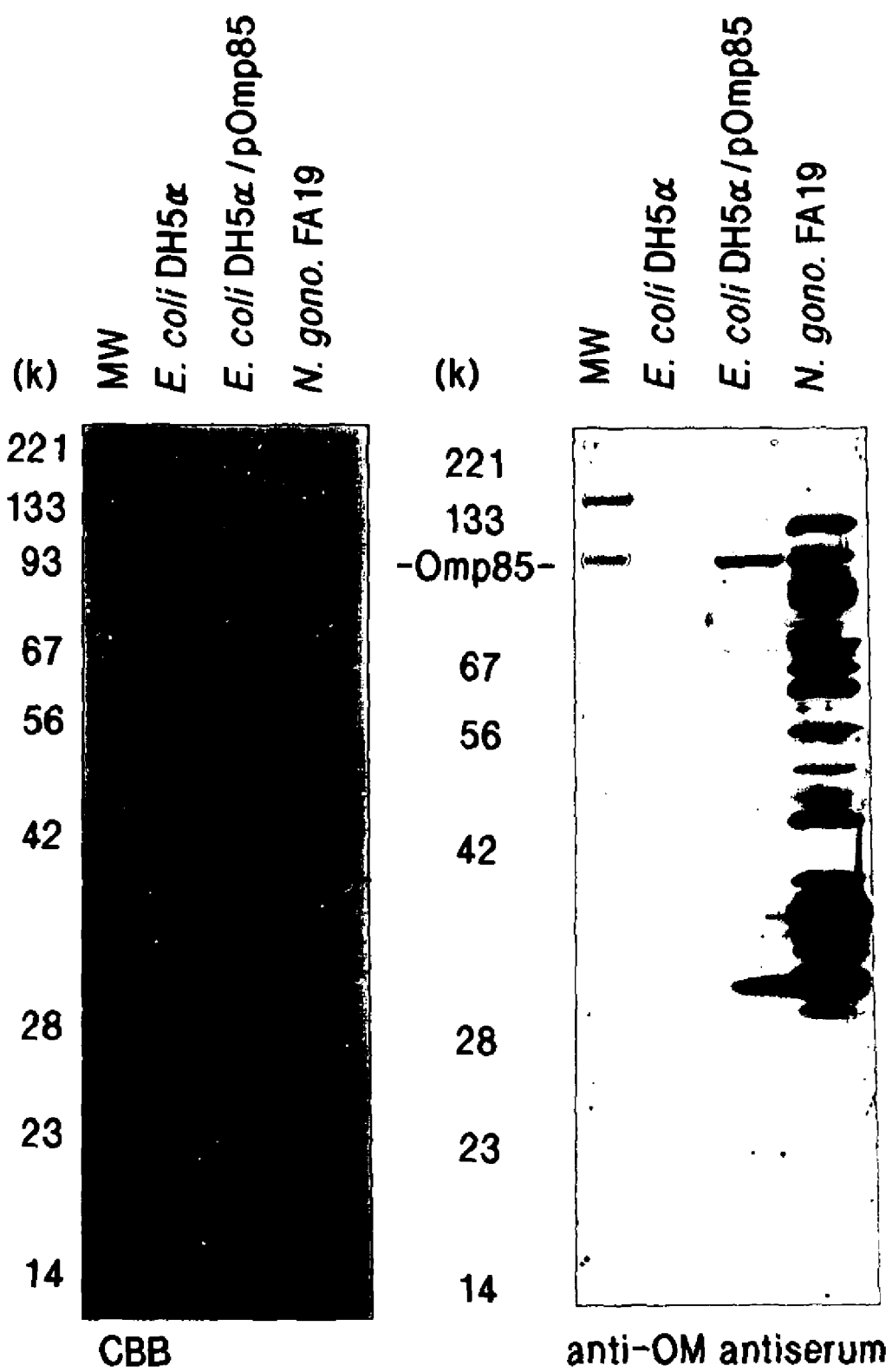
FIG. 1 is a photograph of a sodium dodecyl sulfate polyacrylamide electrophoretic gel (SDS-PAGE) illustrating the identification of recombinant Omp85 produced by *E. coli* DH5α/pOmp85, as described in Example 2. Bacterial cell lysates were separated by SDS-PAGE, stained with Coomassie Brilliant blue (CBB) or transferred to membranes and probed with anti-GC-OM serum. From left to right are *E. coli* DH5α, *E. coli* DH5α/pOmp85, and *N. gonorrhoeae* strain FA19. The location of Omp85 is indicated. Prestained molecular mass markers (MW), were indicated in kilodaltons (kDa).

Western blot analysis of the proteins from *E. coli* DH5α/pOmp85 was performed by separating bacterial cell lysates by SDS-PAGE, staining with COOMASSIE BRILLIANT BLUE™ (CBB) stain or transferring the lysates to membranes and probing with anti-GC-OM serum. The results revealed expression of an approximately 85 kDa polypeptide that was reactive with the anti-GC-OM serum (FIG. 1).

Figure 3:
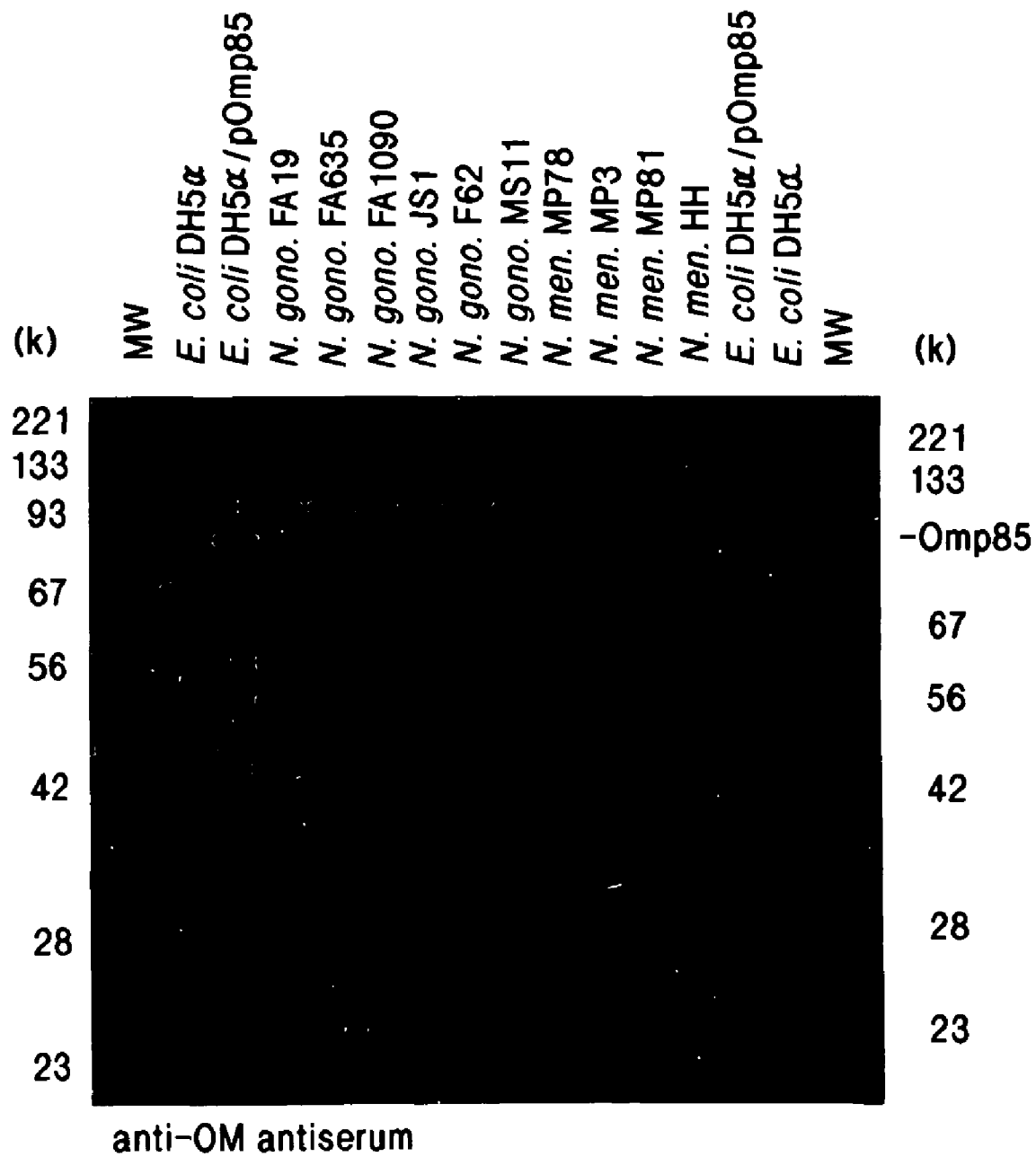
FIG. 3 is a photograph of a Western blot that illustrates the identification of Omp85 in *N. gonorrhoeae* strains FA19, FA635, FA1090, JS1, F62 and MS11LosA and *N. meningitidis* strains MP78, MP3, MP81 and HH by Western blot analysis with anti-GC-OM serum. *E. coli* DH5α and *E. coli* DH5α/pOmp85 were used as negative and positive controls. Prestained molecular mass markers (MW) were indicated in kDa.

Anti-GC-OM serum was reacted in Western blot analysis with total cell proteins from six representative strains of *N. gonorrhoeae* and four strains of *N. meningitidis*. Whole cell lysates of *E. coli* DH5α, *E. coli* DH5α/pOmp85, and *N. gonorrhoeae* strains FA19, FA635, FA1090, JS1, F62 and MS 11LosA and *N. meningitidis* strains MP78, MP3, MP81 and HH were separated by 12.5% SDS-PAGE, blotted and probed with the anti-GC-OM serum. An immunoreactive, approximately 85 kDa protein band was detected in all strains of *N. gonorrhoeae* and *N. meningitidis* (FIG. 3), but not in the control *E. coli* DH5α.

B. Southern Analysis

The Southern analyses are performed as follows. Chromosomal DNA was obtained by phenol extraction (Moore D., "Preparation and analysis of DNA", in: Ausubel F M, et al., eds. Current Protocols in Molecular Biology. New York: John Wiley and Sons, (1997): 2.1.1-2.1.3) and then digested with various endonucleases. Digested DNA was electrophoretically separated on a 1% agarose gel and the DNA transferred to nitrocellulose with the BIO-RAD™ Model 785 vacuum blotter according to instructions and Southern (Southern E., *J. Mol. Biol.*, 98: 503-510 (1975)). Probe DNA was extracted from agarose gels using Bio 101 glassmilk (Vista, Calif.). The probe was labeled and the blot probed with the AMERSHAM ECL™ system (Arlington Heights, Ill.).

Figure 4:
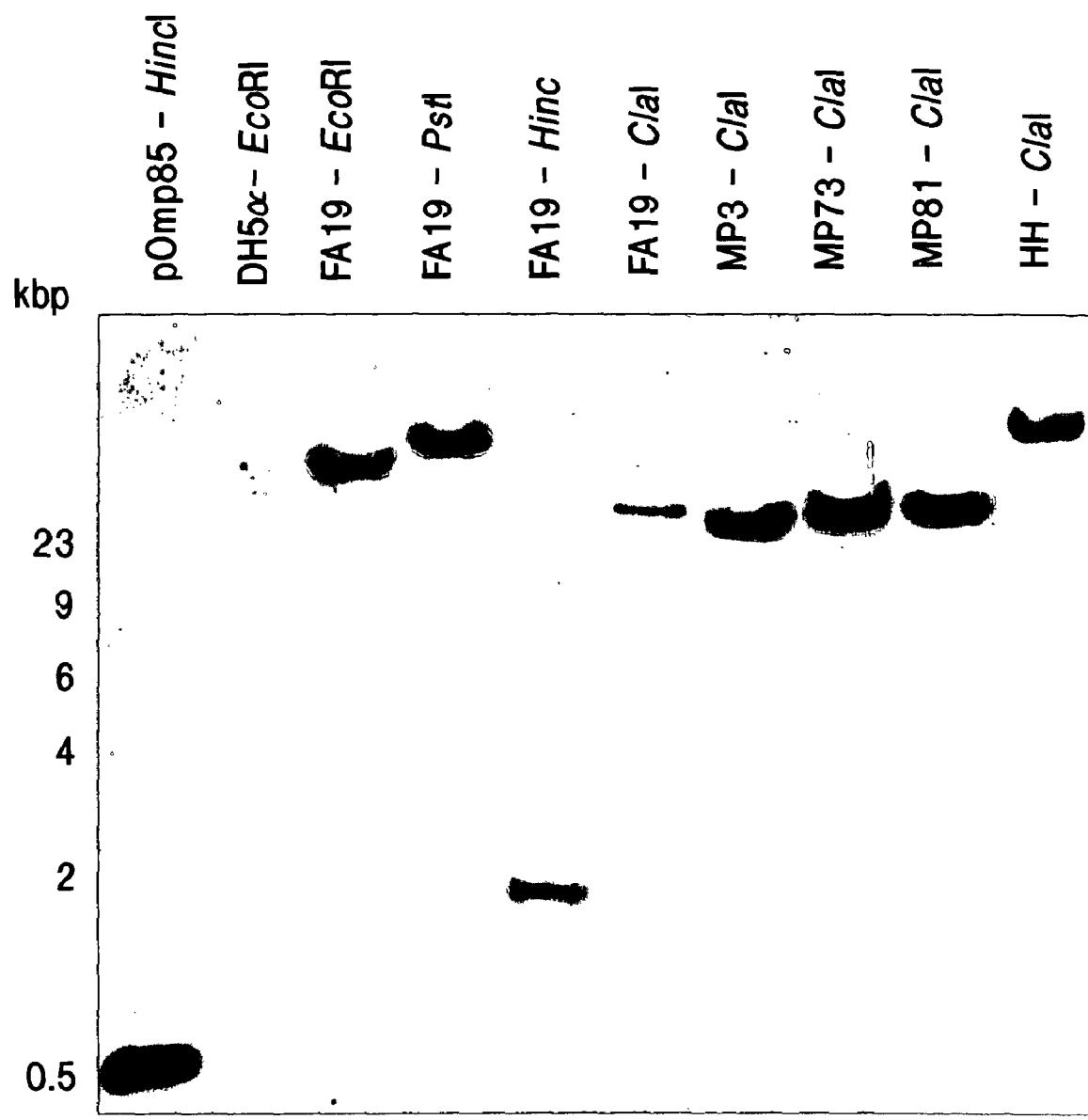
FIG. 4 is a photograph of a Southern blot that illustrates the identification of omp85 in genomic DNA from *N. gonorrhoeae* FA19 and *N. meningitidis* strains MP3, MP73, MP81 and HH digested with restriction endonucleases (HincII, EcoRI, PstI, ClaI) and probed with a 688 bp fragment of gonococcal omp85. This fragment was used as a positive control in the first lane. Molecular weight markers are indicated on the left in kilobase pairs. *E. coli* DH5α was used as a negative control.

A Southern blot (FIG. 4) illustrated the identification of omp85 in *N. gonorrhoeae* and *N. meningitidis* by Southern analysis. Genomic DNA from *E. coli* DH5α, *N. gonorrhoeae* FA19 and *N. meningitidis* strains MP3, MP73, MP81 and HH were digested with restriction endonucleases (HincII, EcoRI, PstI, ClaI). Blots of the separated DNA digests were probed with a 688 bp fragment of gonococcal omp85 that extended from the most 3' HincII site of omp85 to a HincII site in the vector near the 3' end of the cloned gene. This fragment was used as a positive control.

In *N. gonorrhoeae* strain FA19 and in all of the *N. meningitidis* strains, the omp85 probe hybridized with a single DNA band. A single band was also identified in gonococcal strains FA635, FA1090, JS1, F62, and MS11 (data not shown). These results suggested that omp85 was conserved as a single copy in pathogenic *Neisseria*. Sequence data indicated that HincII cleaved omp85 internally at three sites. The probe hybridized to a fragment larger than itself in the HincII digest of gonococcal DNA (FA19-HincII). The genomic fragment resulted from an internal and external HincII cleavage; the probe lacked the flanking gonococcal sequence containing the external HincII site. The genomic HincII band that hybridized to the probe was probably derived from a single copy of the omp85 gene since it is unlikely that duplicate copies of the gene would have identically-located HincII sites, generating fragments of identical size.

The enzyme PstI cleaved 309 base pairs from the 5' end of omp85. The single fragment of PstI-digested gonococcal genomic DNA (FA19-PstI) which hybridized with the probe probably contained a single copy of the gene. It is possible, but unlikely, that the PstI fragments contained approximately 2 kbp segments of omp85 in inverted orientations at each end of the approximately 8 kbp fragment. Sequence data indicated that the enzymes ClaI and EcoRI did not cleave within omp85. The omp85 probe hybridized to single bands of similar size in the ClaI digested DNA of both *N. gonorrhoeae* and *N. meningitidis*. These bands suggested a single copy of omp85, since it is unlikely that bands this small (<6 kbp) contained two copies of the approximately 2.3 kbp gene and it is unlikely that the bands represent fragments of identical size from duplicate copies of the gene. Similar results were obtained for gonococcal strains FA635, FA1090, JS1, F62 and MS11 (data not shown). These results support the conclusion that omp85 is conserved as a single copy in pathogenic *Neisseria*.

EXAMPLE 5

Similarity to Known Proteins

The non-redundant Genbank CDS database was searched (Altchul S D. et al., *J. Mol. Biol.*, 215: 403-407 (1990)) for proteins similar to gonococcal Omp85. The *H. influenzae* D-15-Ag was 31.5% identical and 61.4% similar (identical plus conserved) to gonococcal Omp85. The *P. multocida* Oma87 was 31.6% identical and 61.3% similar to Omp85. Several hypothetical proteins with similarity to Omp85 were identified. A *Brucella abortus* hypothetical protein (Genbank accession #U51683, Bearden, et al., unpublished) was 24.3% identical and 54.2% similar. A hypothetical *E. coli* protein (Genbank accession #U70214, Schramm, et al., unpublished) was 33% identical and 62% similar to Omp85. The gonococcal Omp85 was also similar to hypothetical proteins of *Helicobacter pylori* (Genbank assession # AE001178-Tomb J F. et al., *Nature*, 388: 539-547 (1997)), 23% identical and 51% similar, and *Borrelia burgdorferi* (Genbank assession

AE001178-Fraser C M. et al., *Nature*, 390: 580-586 (1997)), 18% identical and 46% similar.

EXAMPLE 6

Gene Organization and Flanking Genes

Several hundred base pairs of the DNA flanking the omp85 ORFs of both *N. gonorrhoeae* and *N. meningitidis* were sequenced. For both *N. gonorrhoeae* and *N. meningitidis*, a gene similar to ompH of *Salmonella typhimurium* (Kosk P. et al, *J. Biol. Chem.*, 264:18973-18980 (1989)) was identified approximately 65 base pairs 3' of the omp85 ORF. A gene similar to ompH has also been identified in the same relative position in *H. influenzae* (Fleischmann, R D et al, *Science*, 269: 496-512 (1995)) and *P. multocida*. In *H. influenzae*, a gene encoding a hypothetical protein, HI0918, was located 5' of the D-15-Ag gene (Fleischmann, R D et al, *Science*, 269: 496-512 (1995)). A gene homologous to the HI0918 gene was identified at the same relative position in *N. gonorrhoeae*. These results indicated that the gene arrangement around omp85 homologs was notably conserved.

EXAMPLE 7

Presence in *Neisseriae* and Other Species

Western blot analysis was used to determine if proteins similar to Omp85 were produced by commensal *Neisseriae* and by other Gram negative species. To allow more specific immunological analysis, an Omp85-specific polyvalent rabbit sera was produced through use of a fusion protein in which the first 200 amino acids of the gonococcal Omp85 were genetically fused to maltose binding protein (MBP).

A. Production of a MBP/Omp85 Fusion Protein

Fragments of gonococcal Omp85 were genetically fused to MBP, affinity purified and used to produce Omp85-specific antiserum. Tsp509I digested omp85 from pOmp85 was ligated into the EcoRI digested, maltose binding protein fusion vector, pMAL-c2 (New England Biolabs, Beverly, Mass.). Sequence analysis had revealed that this could result in the fusion of several different omp85 fragments in frame with malE in pMAL-c2. The ligated DNA was transformed into *E. coli* DH5α and the transformants were screened for the expression of Omp85 antigens with the anti-OM serum. A number of immunoreactive clones were identified and characterized. The plasmid in the most immunoreactive of these was designated pMO4 and determined by sequence analysis to express a fusion of MBP with the first 181 amino acids of Omp85. The MBP/Omp85 fusion protein was affinity purified from *E. coli* DH5α/pMO4 as previously described (Marchion D C et al, *Mol. Microbiol.*, 6: 231-240 (1997)).

B. Raising of Anti-Sera

Purified MBP/Omp85 was used to raise an anti-Omp85 sera in New Zealand white rabbits. The rabbits were initially immunized with 1 mg of protein in Freund's complete adjuvant administered subcutaneously. Two weeks later 1 mg was administered subcutaneously in Freund's incomplete adjuvant. The rabbits then received intravenous injections of 0.1 mg every two weeks for eight weeks. Sera was collected and absorbed (1:1) with a lysed culture of *E. coli*/pMal-c2 induced with 1 mM IPTG for 1 hour. The resulting rabbit serum was designated anti-Omp85.

C. Western Analysis of Representative Strains of *N. Gonorrhoeae* and *N. Meningitis*

Figure 6:
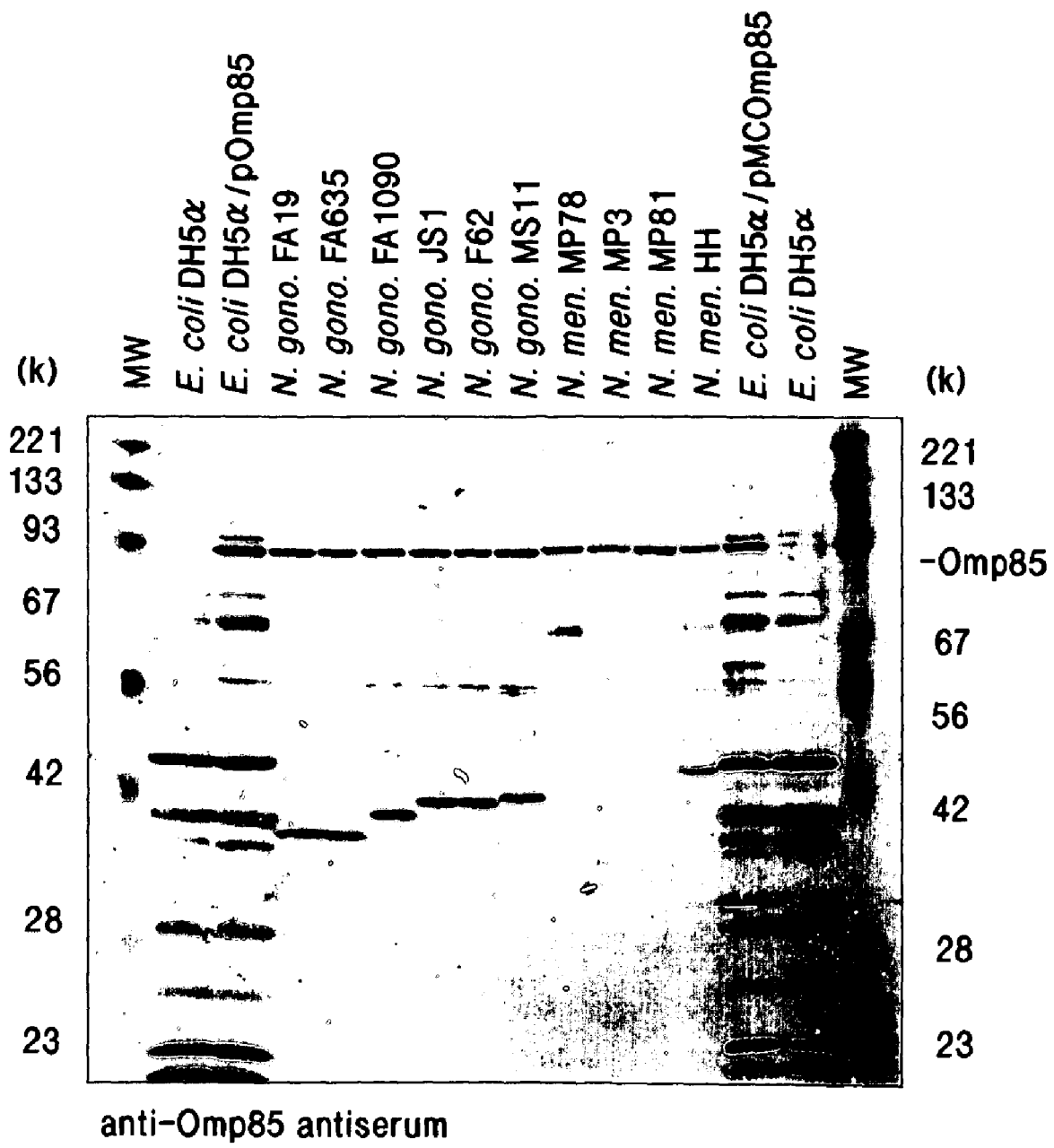
FIG. 6 is a photograph of a Western blot that illustrates the identification of Omp85 in *N. gonorrhoeae* strains FA19, FA635, FA1090, JS1, F62 and MS11LosA and *N. meningitidis* strains MP78, MP3, MP81 and HH by Western blot analysis with anti-Omp85, as described in Example 7. *E. coli* DH5α, *E. coli* DH5α/pOmp85 and *E. coli* DH5α/pMCOmp85 were used as negative and positive controls. Prestained molecular mass markers (MW) were indicated in kDa.

The anti-Omp85 serum was used to probe Western blots containing cell lysates of *E. coli* DH5α, *E. coli* DH5α/pOmp85 and representative strains of *N. gonorrhoeae* and *N. meningitidis* (FIG. 6). Whole cell lysates of *E. coli* DH5α, *E. coli* DH5α/pOmp85, *N. gonorrhoeae* strains FA19, FA635, FA1090, JS1, F62 and MS11LosA, *N. meningitidis* strains MP78, MP3, MP81 and HH, and *E. coli* DH5α/pMCOmp85 were separated by 12.5% SDS-PAGE, blotted and probed with the anti-Omp85 serum.

The anti-Omp85 serum reacted with the recombinant Omp85 produced by *E. coli* DH5α/pOmp85 and with proteins of approximately 85 kDa in all of the *N. gonorrhoeae* and *N. meningitidis* strains tested. These results indicated that Omp85 was conserved in the pathogenic *Neisseriae*. Presorption of the antiserum removed the majority of non-specific antibodies, but complete removal of all reactive antibody is not possible, thus, some reactive bands can be seen in the *E. coli* lanes of FIG. 6. Reactive bands in the 35 kDa-42 kDa range in *N. gonorrhoeae* lanes are Por proteins, which non-specifically bind protein-A. Meningococcal Pors do not bind protein-A as strongly (data not shown).

D. Western Analysis of Commensal *Nesseriae* and Other Gram Negative Species

The anti-Omp85 was also used to probe Western blots containing cell lysates of commensal *Nesseriae* and several other Gram negative species. Whole cell lysates of *E coli* DH5α, *E. coli* DH5α/pOmp85, *N. gonorrhoeae* FA19 (A), *Neisseria pharyngis* (A), *Neisseria cinerea* (A), *Neisseria lactamica* (B), *Neisseria mucosae* (B), *Neisseria flavescens* (C), *Neisseria animalis* (C), *Neisseria denitrificans* (C), *Moraxella catarrhalis* (D), *Klebsiella pneumoniae*, *Pseudomonas aeruginosa*, and *N. meningitidis* HH (A) were separated in a 12.5% SDSαPAGE gel, blotted and probed with anti-Omp85. In a separate experiment, whole cell lysates of *E. coli* DH5α, *E. coli* DH5α/pOmp85, *N. gonorrhoeae* FA19, *Salmonella typhimurium*, *Shigella flexneri*, *E. coli* strains 35150 (enterohemorrhagic-EHEC), 35401 (enterotoxigenic-ETEC), 43887 (enteropathogenic-EPEC), 43892 (enteroinvasive-EIEC) and *N. meningitidis* were separated in a 12.5% SDS-PAGE gel, blotted and probed with anti-Omp85.

Two SDS-PAGE (FIGS. 7A and 7B) illustrate the distribution of Omp85 in pathogenic and commensal *Neisseria* (relationship areas A, B, C, and D) and related Gram negative bacteria. Omp85 homologs were identified in all of the commensal *Neisserial* species tested. This suggested that Omp85 was conserved among all the *Neisserial* species. The anti-Omp85 serum failed to identify any Omp85 homologs in *Moraxella catarrhalis* which is closely related to the *Neisseriae* (Rossau R. et al, *Int. J. Syst. Bacteriol.*, 39: 185-198 (1989)). Southern analysis confirmed the absence of an omp85 homolog in this species (data not shown). The serum failed to identify any Omp85 homologs in *Klebsiella pneumoniae*, *Pseudomonas aeruginosa*, *Salmonella typhimurium*, *Shigella flexneri* and four pathogenic strains of *E. coli* tested.

EXAMPLE 8

Gonococcal Cell Adherence Assay

Gonococcal cell adherence assays were performed to evaluate the effect of antiserum specific for outer membrane protein 85 (Omp85) on the ability of gonococcal strains MS11LOSA (MS11) and FA19 to bind to Chang epithelial cells. Fab fragments were prepared from antiserum to the first 178 amino acids of Omp85 (SEQ ID NO: 2), hyperimmune antiserum to bovine serum albumin (BSA) and normal rabbit serum (NRS) and added at 1 µg, 10 µgs or 100 µgs per ml to wells containing a confluent layer of Chang conjunctiva cells. Approximately $2.5 \times 10^5$ bacteria (*N. gonorrhoeae* strain MS11 or FA19) were added to each well and allowed to adhere for 3 hours. Following fixation and immunogold/silver staining, the number of adherent gonococci was determined for 22 cells. The lowest and highest numbers were discarded and the average number of bacteria/cell were determined. The resulting data is reported in the bar graph of FIG. 8, indicating that Omp85-specific antibody was able to bind to the surface of the bacteria and interfere with the ability of the bacteria to adhere to the Chang epithelial cells.

All publications cited in this specification are indicative of the level of skill of those in the art to which this application pertains and are incorporated herein by reference herein. While the invention has been described with reference to a particularly preferred embodiment, it will be appreciated that modifications can be made without departing from the spirit of the invention. Such modifications are intended to fall within the scope of the appended claims.

---

What is claimed is:

1. An immunogenic composition comprising an isolated polypeptide comprising an amino acid sequence having 95% or greater sequence identity with the amino acid sequence of SEQ ID NO: 4, and a pharmaceutically acceptable carrier, wherein said polypeptide in said composition induces antibodies in a mammal that bind to said amino acid sequence of SEQ ID NO: 4 and that interfere with adherence of *Neisseria gonorrhoeae* as measured by the gonococcal cell adherence assay, wherein said isolated polypeptide is in a purified form.

* * * * *

UNITED STATES PATENT AND TRADEMARK OFFICE
CERTIFICATE OF CORRECTION

PATENT NO. : 7,794,733 B2  Page 1 of 1
APPLICATION NO. : 10/606618
DATED : September 14, 2010
INVENTOR(S) : Ralph C. Judd and D. Scott Manning It is certified that error appears in the above-identified patent and that said Letters Patent is hereby corrected as shown below:

Title Page, Item (75) Inventors: replace "Missoula, MO" with -- Missoula, MT -- after D. Scott Manning.

Signed and Sealed this

Sixteenth Day of November, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 2379
<212> TYPE: DNA
<213> ORGANISM: Neisseria gonorrhoeae
<220> FEATURE:
<221> NAME/KEY: CDS
<222> LOCATION: (1)..(2376)
<223> OTHER INFORMATION:

<400> SEQUENCE: 1

```
atg aaa ctg aaa cag att gcc tcc gca ctg atg atg ttg ggc ata tcg      48
Met Lys Leu Lys Gln Ile Ala Ser Ala Leu Met Met Leu Gly Ile Ser
1               5                   10                  15 cct ttg gca ttt gcc gac ttc acc atc caa gac atc cgt gtc gaa ggc      96
Pro Leu Ala Phe Ala Asp Phe Thr Ile Gln Asp Ile Arg Val Glu Gly
            20                  25                  30 ttg cag cgt acc gag ccg agc acc gta ttc aac tac ctg ccc gtc aaa     144
Leu Gln Arg Thr Glu Pro Ser Thr Val Phe Asn Tyr Leu Pro Val Lys
        35                  40                  45 gtc ggc gac acc tac aac gac aca cac ggc agt gcc atc atc aaa agc     192
Val Gly Asp Thr Tyr Asn Asp Thr His Gly Ser Ala Ile Ile Lys Ser
    50                  55                  60 ctg tac gcc acc ggt ttc ttt gac gac gta cga gtc gaa act gcg gac     240
Leu Tyr Ala Thr Gly Phe Phe Asp Asp Val Arg Val Glu Thr Ala Asp
65                  70                  75                  80 ggg ctg ctt ctg acc gtt atc gta tgc cct acc atc ggc tcg ctc         288
Gly Leu Leu Leu Thr Val Ile Val Cys Pro Thr Ile Gly Ser Leu
                85                  90                  95 aac atc acc ggc gcc aaa atg ctg cag aac gac gcc atc aag aaa aac     336
Asn Ile Thr Gly Ala Lys Met Leu Gln Asn Asp Ala Ile Lys Lys Asn
            100                 105                 110 ctc gaa tcg ttc ggg ctg gcg cag tcg caa tac ttt aat cag gcg aca     384
Leu Glu Ser Phe Gly Leu Ala Gln Ser Gln Tyr Phe Asn Gln Ala Thr
        115                 120                 125 ctc aac cag gca gtc gcc ggc ctg aaa gaa gaa tat ctc ggg cgc ggc     432
Leu Asn Gln Ala Val Ala Gly Leu Lys Glu Glu Tyr Leu Gly Arg Gly
    130                 135                 140 aaa ctc aat atc caa atc acg ccc aaa gta acc aaa ctc gcc cgc aac     480
Lys Leu Asn Ile Gln Ile Thr Pro Lys Val Thr Lys Leu Ala Arg Asn
145                 150                 155                 160 cgc gtc gac atc gac atc acg att gac gag ggc aaa tcc gcc aaa atc     528
Arg Val Asp Ile Asp Ile Thr Ile Asp Glu Gly Lys Ser Ala Lys Ile
                165                 170                 175 acc gac atc gaa ttt gaa ggc aac caa gtc tat tcc gac cgc aaa ctg     576
Thr Asp Ile Glu Phe Glu Gly Asn Gln Val Tyr Ser Asp Arg Lys Leu
            180                 185                 190 atg cgg cag atg tcg ctg acc gaa ggc ggc att tgg aca tgg ctg aca     624
Met Arg Gln Met Ser Leu Thr Glu Gly Gly Ile Trp Thr Trp Leu Thr
        195                 200                 205 cga agc gac cgg ttc gac cgc cag aaa ttc gcc caa gac atg gaa aaa     672
Arg Ser Asp Arg Phe Asp Arg Gln Lys Phe Ala Gln Asp Met Glu Lys
```

-continued

```
                    210                 215                 220
gta acc gac ttc tac cag aac aac ggc tac ttc gat ttc cgt atc ctc     720
Val Thr Asp Phe Tyr Gln Asn Asn Gly Tyr Phe Asp Phe Arg Ile Leu
225                 230                 235                 240 gat acc gac atc caa acc aac gaa gac aaa acc agg cag acc atc aaa     768
Asp Thr Asp Ile Gln Thr Asn Glu Asp Lys Thr Arg Gln Thr Ile Lys
                    245                 250                 255 atc acc gtc cac gaa ggc gga cgt ttc cgc tgg ggc aaa gtg tcg att     816
Ile Thr Val His Glu Gly Gly Arg Phe Arg Trp Gly Lys Val Ser Ile
                260                 265                 270 gaa ggc gac acc aac gaa gtc ccc aag gcc gaa ctg gaa aaa ctg ctg     864
Glu Gly Asp Thr Asn Glu Val Pro Lys Ala Glu Leu Glu Lys Leu Leu
            275                 280                 285 acc atg aag ccc ggc aaa tgg tac gaa cgc cag cag atg acc gcc gtt     912
Thr Met Lys Pro Gly Lys Trp Tyr Glu Arg Gln Gln Met Thr Ala Val
        290                 295                 300 ttg ggt gag att cag aac cgc atg ggc tcg gca ggc tac gca tac agc     960
Leu Gly Glu Ile Gln Asn Arg Met Gly Ser Ala Gly Tyr Ala Tyr Ser
305                 310                 315                 320 gaa atc agc gta cag ccg ctg ccg aac gcc gga acc aaa acc gtc gat    1008
Glu Ile Ser Val Gln Pro Leu Pro Asn Ala Gly Thr Lys Thr Val Asp
                325                 330                 335 ttc gtc ctg cac atc gaa ccg ggc aga aaa atc tac gtc aac gaa atc    1056
Phe Val Leu His Ile Glu Pro Gly Arg Lys Ile Tyr Val Asn Glu Ile
                340                 345                 350 cac atc acc ggc aac aac aaa acc cgc gac gaa gtc gtg cgc cgc gaa    1104
His Ile Thr Gly Asn Asn Lys Thr Arg Asp Glu Val Val Arg Arg Glu
            355                 360                 365 ttg cgc caa atg gaa tcc gcg cct tac gac acc tcc aag ctg caa cgc    1152
Leu Arg Gln Met Glu Ser Ala Pro Tyr Asp Thr Ser Lys Leu Gln Arg
370                 375                 380 tcc aaa gag cgc gtc gag ctt ttg ggc tac ttc gac aac gta cag ttt    1200
Ser Lys Glu Arg Val Glu Leu Leu Gly Tyr Phe Asp Asn Val Gln Phe
385                 390                 395                 400 gat gcc gtc ccg ctt gcc ggt acg ccc gac aaa gtc gat ttg aac atg    1248
Asp Ala Val Pro Leu Ala Gly Thr Pro Asp Lys Val Asp Leu Asn Met
                405                 410                 415 agc ctg acc gaa cgt tcc acc ggc tcg ctc gac ttg agc gcg ggc tgg    1296
Ser Leu Thr Glu Arg Ser Thr Gly Ser Leu Asp Leu Ser Ala Gly Trp
                420                 425                 430 gtt cag gat acc ggc ttg gtc atg tcc gcc ggc gta tcg cag gac aac    1344
Val Gln Asp Thr Gly Leu Val Met Ser Ala Gly Val Ser Gln Asp Asn
            435                 440                 445 ctg ttc ggt acg ggc aag tcg gcc gcc ctg cgc gcc tcg cga agc aaa    1392
Leu Phe Gly Thr Gly Lys Ser Ala Ala Leu Arg Ala Ser Arg Ser Lys
450                 455                 460 acc acg ctc aac ggc tcg ctg tcg ttt acc gac ccg tac ttc acg gca    1440
Thr Thr Leu Asn Gly Ser Leu Ser Phe Thr Asp Pro Tyr Phe Thr Ala
465                 470                 475                 480 gac ggg gtc agc ctg ggc tac gat att tac gga aaa gcc ttc gac ccg    1488
Asp Gly Val Ser Leu Gly Tyr Asp Ile Tyr Gly Lys Ala Phe Asp Pro
                485                 490                 495 cgc aaa gca tcg acc agc gtc aaa caa tat aaa acc acc gcc ggc        1536
Arg Lys Ala Ser Thr Ser Val Lys Gln Tyr Lys Thr Thr Ala Gly
                500                 505                 510 ggc ggc gta agg atg ggt atc ccc gtt acc gaa tac gac cgc gtc aat    1584
Gly Gly Val Arg Met Gly Ile Pro Val Thr Glu Tyr Asp Arg Val Asn
            515                 520                 525 ttc ggg ctg gcg gcg gaa cac ctg acc gtc aac acc tac aac aaa gca    1632
```

-continued

```
Phe Gly Leu Ala Ala Glu His Leu Thr Val Asn Thr Tyr Asn Lys Ala
        530                 535                 540 ccc aaa cgc tat gcc gac ttt atc aaa caa tac ggc aaa acc gac ggc      1680
Pro Lys Arg Tyr Ala Asp Phe Ile Lys Gln Tyr Gly Lys Thr Asp Gly
545                 550                 555                 560 gca gac ggc agc ttc aaa ggc ctg ctg tac aaa ggc act gtc ggc tgg      1728
Ala Asp Gly Ser Phe Lys Gly Leu Leu Tyr Lys Gly Thr Val Gly Trp
                565                 570                 575 ggg cgc aac aag acc gac agc gcc tta tgg ccg acg cgc ggc tac ctg      1776
Gly Arg Asn Lys Thr Asp Ser Ala Leu Trp Pro Thr Arg Gly Tyr Leu
            580                 585                 590 acc ggc gta aat gcc gaa atc gcc ctg ccc ggc agc aaa ctg caa tac      1824
Thr Gly Val Asn Ala Glu Ile Ala Leu Pro Gly Ser Lys Leu Gln Tyr
        595                 600                 605 tac tcc gcc acc cac aac caa acc tgg ttc ttc ccc tta agc aaa acc      1872
Tyr Ser Ala Thr His Asn Gln Thr Trp Phe Phe Pro Leu Ser Lys Thr
    610                 615                 620 ttc acg ctg atg ctc ggc ggc gaa gtc ggc att gcg ggc ggc tac ggc      1920
Phe Thr Leu Met Leu Gly Gly Glu Val Gly Ile Ala Gly Gly Tyr Gly
625                 630                 635                 640 aga acc aaa gaa atc ccc ttc ttt gaa aac ttc tac ggc ggc ggc ctg      1968
Arg Thr Lys Glu Ile Pro Phe Phe Glu Asn Phe Tyr Gly Gly Gly Leu
                645                 650                 655 ggt tcg gtg cgc ggc tac gaa agc ggc acg ctc ggc ccg aaa gtg tat      2016
Gly Ser Val Arg Gly Tyr Glu Ser Gly Thr Leu Gly Pro Lys Val Tyr
            660                 665                 670 gac gaa tac ggc gaa aaa atc agc tac ggc ggc aac aaa aaa gcc aac      2064
Asp Glu Tyr Gly Glu Lys Ile Ser Tyr Gly Gly Asn Lys Lys Ala Asn
        675                 680                 685 gtc tcc gcc gag ctg ctc ttc ccg atg ccc ggt gcg aaa gac gca cgc      2112
Val Ser Ala Glu Leu Leu Phe Pro Met Pro Gly Ala Lys Asp Ala Arg
    690                 695                 700 acc gtc cgc ctg agc ctg ttt gcc gac gca ggc agc gtg tgg gac ggc      2160
Thr Val Arg Leu Ser Leu Phe Ala Asp Ala Gly Ser Val Trp Asp Gly
705                 710                 715                 720 aga acc tat acc gcc gcc gaa aac ggt aac aac aaa tcg gtt tac tcg      2208
Arg Thr Tyr Thr Ala Ala Glu Asn Gly Asn Asn Lys Ser Val Tyr Ser
                725                 730                 735 gaa aac gcg cat aaa tcc acc ttt acc aac gaa ttg cgc tat tcc gcc      2256
Glu Asn Ala His Lys Ser Thr Phe Thr Asn Glu Leu Arg Tyr Ser Ala
            740                 745                 750 ggc ggc gcg gtt acc tgg ctc tcg cct ttg ggc ccg atg aaa ttc atc      2304
Gly Gly Ala Val Thr Trp Leu Ser Pro Leu Gly Pro Met Lys Phe Ile
        755                 760                 765 tac gcc tac ccg ctg aag aaa aaa ccg gaa gac gaa atc caa cgc ttc      2352
Tyr Ala Tyr Pro Leu Lys Lys Lys Pro Glu Asp Glu Ile Gln Arg Phe
    770                 775                 780 caa ttc cag ctc ggc acg acg ttc taa                                  2379
Gln Phe Gln Leu Gly Thr Thr Phe
785                 790

<210> SEQ ID NO 2
<211> LENGTH: 792
<212> TYPE: PRT
<213> ORGANISM: Neisseria gonorrhoeae

<400> SEQUENCE: 2

Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
```

-continued

```
                 20                  25                  30
Leu Gln Arg Thr Glu Pro Ser Thr Val Phe Asn Tyr Leu Pro Val Lys
             35                  40                  45
Val Gly Asp Thr Tyr Asn Asp Thr His Gly Ser Ala Ile Ile Lys Ser
 50                  55                  60
Leu Tyr Ala Thr Gly Phe Phe Asp Asp Val Arg Val Glu Thr Ala Asp
 65                  70                  75                  80
Gly Leu Leu Leu Leu Thr Val Ile Val Cys Pro Thr Ile Gly Ser Leu
                 85                  90                  95
Asn Ile Thr Gly Ala Lys Met Leu Gln Asn Asp Ala Ile Lys Lys Asn
                100                 105                 110
Leu Glu Ser Phe Gly Leu Ala Gln Ser Gln Tyr Phe Asn Gln Ala Thr
             115                 120                 125
Leu Asn Gln Ala Val Ala Gly Leu Lys Glu Glu Tyr Leu Gly Arg Gly
        130                 135                 140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                165                 170                 175
Thr Asp Ile Glu Phe Glu Gly Asn Gln Val Tyr Ser Asp Arg Lys Leu
                180                 185                 190
Met Arg Gln Met Ser Leu Thr Glu Gly Gly Ile Trp Thr Trp Leu Thr
             195                 200                 205
Arg Ser Asp Arg Phe Asp Arg Gln Lys Phe Ala Gln Asp Met Glu Lys
        210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Arg Gln Thr Ile Lys
                245                 250                 255
Ile Thr Val His Glu Gly Gly Arg Phe Arg Trp Gly Lys Val Ser Ile
                260                 265                 270
Glu Gly Asp Thr Asn Glu Val Pro Lys Ala Glu Leu Glu Lys Leu Leu
             275                 280                 285
Thr Met Lys Pro Gly Lys Trp Tyr Glu Arg Gln Gln Met Thr Ala Val
        290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Gly Thr Lys Thr Val Asp
                325                 330                 335
Phe Val Leu His Ile Glu Pro Gly Arg Lys Ile Tyr Val Asn Glu Ile
                340                 345                 350
His Ile Thr Gly Asn Asn Lys Thr Arg Asp Glu Val Val Arg Arg Glu
             355                 360                 365
Leu Arg Gln Met Glu Ser Ala Pro Tyr Asp Thr Ser Lys Leu Gln Arg
        370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
                420                 425                 430
Val Gln Asp Thr Gly Leu Val Met Ser Ala Gly Val Ser Gln Asp Asn
             435                 440                 445
```

```
Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
                485                 490                 495

Arg Lys Ala Ser Thr Ser Val Lys Gln Tyr Lys Thr Thr Ala Gly
                500                 505                 510

Gly Gly Val Arg Met Gly Ile Pro Val Thr Glu Tyr Asp Arg Val Asn
            515                 520                 525

Phe Gly Leu Ala Ala Glu His Leu Thr Val Asn Thr Tyr Asn Lys Ala
530                 535                 540

Pro Lys Arg Tyr Ala Asp Phe Ile Lys Gln Tyr Gly Lys Thr Asp Gly
545                 550                 555                 560

Ala Asp Gly Ser Phe Lys Gly Leu Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Asn Lys Lys Ala Asn
                675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735

Glu Asn Ala His Lys Ser Thr Phe Thr Asn Glu Leu Arg Tyr Ser Ala
            740                 745                 750

Gly Gly Ala Val Thr Trp Leu Ser Pro Leu Gly Pro Met Lys Phe Ile
        755                 760                 765

Tyr Ala Tyr Pro Leu Lys Lys Pro Glu Asp Glu Ile Gln Arg Phe
770                 775                 780

Gln Phe Gln Leu Gly Thr Thr Phe
785                 790
```

<210> SEQ ID NO 3
<211> LENGTH: 2394
<212> TYPE: DNA
<213> ORGANISM: Neisseria meningitidis
<220> FEATURE:
<221> NAME/KEY: CDS
<222> LOCATION: (1)..(2391)
<223> OTHER INFORMATION:

<400> SEQUENCE: 3

```
atg aaa ctg aaa cag att gct tcc gca ctg atg atg ttg ggc ata tcg        48
Met Lys Leu Lys Gln Ile Ala Ser Ala Leu Met Met Leu Gly Ile Ser
1               5                   10                  15 cct ttg gca ttt gcc gac ttc acc atc caa gac atc cgt gtc gaa ggc        96
Pro Leu Ala Phe Ala Asp Phe Thr Ile Gln Asp Ile Arg Val Glu Gly
            20                  25                  30 ttg cag cgt acc gag ccg agc acc gta ttc aac tac ctg ccc gtc aaa       144
Leu Gln Arg Thr Glu Pro Ser Thr Val Phe Asn Tyr Leu Pro Val Lys
        35                  40                  45 gtc ggc gat acc tac aac gac aca cac ggc agt gcc atc atc aaa agc       192
Val Gly Asp Thr Tyr Asn Asp Thr His Gly Ser Ala Ile Ile Lys Ser
    50                  55                  60 ctg tac gcc acc ggt ttc ttt gac gac gta cgc gtc gaa act gcg gac       240
Leu Tyr Ala Thr Gly Phe Phe Asp Asp Val Arg Val Glu Thr Ala Asp
65                  70                  75                  80 ggg cag ctc ctg ctg acc gtt atc gaa cgc ccc acc atc ggc tcg ctc       288
Gly Gln Leu Leu Leu Thr Val Ile Glu Arg Pro Thr Ile Gly Ser Leu
                85                  90                  95 aac atc acc ggc gca aaa atg ctg caa aac gac gcc att aag aaa aac       336
Asn Ile Thr Gly Ala Lys Met Leu Gln Asn Asp Ala Ile Lys Lys Asn
            100                 105                 110 ctc gaa tcg ttc ggg ctg gcg cag tcg caa tac ttt aat cag gcg aca       384
Leu Glu Ser Phe Gly Leu Ala Gln Ser Gln Tyr Phe Asn Gln Ala Thr
        115                 120                 125 ctc aat cag gca gtc gcc ggc ctg aaa gaa gaa tac ctc ggg cgc ggc       432
Leu Asn Gln Ala Val Ala Gly Leu Lys Glu Glu Tyr Leu Gly Arg Gly
    130                 135                 140 aaa ctc aat atc caa atc acg ccc aaa gta acc aaa ctc gcc cgc aac       480
Lys Leu Asn Ile Gln Ile Thr Pro Lys Val Thr Lys Leu Ala Arg Asn
145                 150                 155                 160 cgc gtc gac atc gac atc acg att gac gag ggc aaa tcc gcc aaa atc       528
Arg Val Asp Ile Asp Ile Thr Ile Asp Glu Gly Lys Ser Ala Lys Ile
                165                 170                 175 acc gac atc gaa ttt gaa ggc aac caa gtc tat tcc gac cgc aaa ctg       576
Thr Asp Ile Glu Phe Glu Gly Asn Gln Val Tyr Ser Asp Arg Lys Leu
            180                 185                 190 atg cgg cag atg tcg ctg acc gaa ggc ggc att tgg aca tgg ctg aca       624
Met Arg Gln Met Ser Leu Thr Glu Gly Gly Ile Trp Thr Trp Leu Thr
        195                 200                 205 cga agc aac caa ttc aac gag cag aaa ttt gcc caa gac atg gaa aaa       672
Arg Ser Asn Gln Phe Asn Glu Gln Lys Phe Ala Gln Asp Met Glu Lys
    210                 215                 220 gta acc gac ttc tac cag aac aac ggc tac ttc gat ttc cgt atc ctc       720
Val Thr Asp Phe Tyr Gln Asn Asn Gly Tyr Phe Asp Phe Arg Ile Leu
225                 230                 235                 240 gat acc gac atc caa acc aac gaa gac aaa acc aag cag acc atc aaa       768
Asp Thr Asp Ile Gln Thr Asn Glu Asp Lys Thr Lys Gln Thr Ile Lys
                245                 250                 255 atc acc gtc cac gaa ggc gga cgt ttc cgt tgg ggc aaa gtc tcc atc       816
Ile Thr Val His Glu Gly Gly Arg Phe Arg Trp Gly Lys Val Ser Ile
            260                 265                 270 gaa ggc gac acc aac gaa gtc ccc aaa gcc gaa ctg gaa aaa ctg ctg       864
Glu Gly Asp Thr Asn Glu Val Pro Lys Ala Glu Leu Glu Lys Leu Leu
        275                 280                 285 acc atg aag ccc ggc aaa tgg tac gaa cgc cag cag atg acc gcc gtt       912
Thr Met Lys Pro Gly Lys Trp Tyr Glu Arg Gln Gln Met Thr Ala Val
    290                 295                 300 ttg ggt gag att cag aac cgc atg ggc tcg gca ggc tac gca tac agc       960
Leu Gly Glu Ile Gln Asn Arg Met Gly Ser Ala Gly Tyr Ala Tyr Ser
305                 310                 315                 320
```

```
gaa atc agc gta cag ccg ctg cca aac gcc gaa acc aaa acc gtc gat    1008
Glu Ile Ser Val Gln Pro Leu Pro Asn Ala Glu Thr Lys Thr Val Asp
            325                 330                 335 ttc gtc ctg cac atc gaa ccg ggc cgg aaa atc tac gtc aac gaa atc    1056
Phe Val Leu His Ile Glu Pro Gly Arg Lys Ile Tyr Val Asn Glu Ile
            340                 345                 350 cac atc acc ggc aac aac aaa acc cgc gac gaa gtc gtg cgc cgc gaa    1104
His Ile Thr Gly Asn Asn Lys Thr Arg Asp Glu Val Val Arg Arg Glu
            355                 360                 365 ttg cgc caa atg gaa tcc gcg cct tac gac acc tcc aag ctg caa cgc    1152
Leu Arg Gln Met Glu Ser Ala Pro Tyr Asp Thr Ser Lys Leu Gln Arg
    370                 375                 380 tcc aaa gag cgc gtc gag ctt ttg ggc tac ttc gac aac gta cag ttt    1200
Ser Lys Glu Arg Val Glu Leu Leu Gly Tyr Phe Asp Asn Val Gln Phe
385                 390                 395                 400 gat gcc gtc ccg ctt gcc ggc aca ccc gac aaa gtc gat ttg aac atg    1248
Asp Ala Val Pro Leu Ala Gly Thr Pro Asp Lys Val Asp Leu Asn Met
                405                 410                 415 agc ctg acc gaa cgt tcc acc ggc tcg ctc gac ttg agc gcg ggc tgg    1296
Ser Leu Thr Glu Arg Ser Thr Gly Ser Leu Asp Leu Ser Ala Gly Trp
            420                 425                 430 gta cag gat acc ggc ctg gtc atg tcc gca ggc gtt tcc caa gac aac    1344
Val Gln Asp Thr Gly Leu Val Met Ser Ala Gly Val Ser Gln Asp Asn
            435                 440                 445 ctg ttc ggt acg ggc aag tcg gcc gcc ctg cgc gcc tca cga agc aaa    1392
Leu Phe Gly Thr Gly Lys Ser Ala Ala Leu Arg Ala Ser Arg Ser Lys
    450                 455                 460 acc acg ctc aac ggc tcg ctg tcg ttt acc gac ccg tac ttc acg gca    1440
Thr Thr Leu Asn Gly Ser Leu Ser Phe Thr Asp Pro Tyr Phe Thr Ala
465                 470                 475                 480 gac ggg gtc agc ctg ggc tac gat gtt tac gga aaa gcc ttc gac ccg    1488
Asp Gly Val Ser Leu Gly Tyr Asp Val Tyr Gly Lys Ala Phe Asp Pro
                485                 490                 495 cgc aaa gca tcg acc agc atc aaa caa tat aaa acc acg gca ggc        1536
Arg Lys Ala Ser Thr Ser Ile Lys Gln Tyr Lys Thr Thr Ala Gly
            500                 505                 510 gca ggc atc cgc atg agc gtg cct gtt acc gaa tac gac cgc gtg aat    1584
Ala Gly Ile Arg Met Ser Val Pro Val Thr Glu Tyr Asp Arg Val Asn
            515                 520                 525 ttc ggt ttg gtg gca gaa cac ctg acc gtc aac acc tac aac aaa gcg    1632
Phe Gly Leu Val Ala Glu His Leu Thr Val Asn Thr Tyr Asn Lys Ala
530                 535                 540 ccc aaa cac tat gcc gac ttt atc aag aaa tac ggc aaa acc gac ggc    1680
Pro Lys His Tyr Ala Asp Phe Ile Lys Lys Tyr Gly Lys Thr Asp Gly
545                 550                 555                 560 aca gac ggc agc ttc aaa ggc tgg ctg tac aaa ggt acc gtc ggc tgg    1728
Thr Asp Gly Ser Phe Lys Gly Trp Leu Tyr Lys Gly Thr Val Gly Trp
                565                 570                 575 ggg cgc aac aaa acc gac agc gcg tta tgg ccg acg cgc ggc tac ctg    1776
Gly Arg Asn Lys Thr Asp Ser Ala Leu Trp Pro Thr Arg Gly Tyr Leu
            580                 585                 590 acg ggc gtg aac gcc gaa atc gcc ctg ccc ggc agc aaa ctg caa tac    1824
Thr Gly Val Asn Ala Glu Ile Ala Leu Pro Gly Ser Lys Leu Gln Tyr
            595                 600                 605 tac tcc gcc acc cac aac caa acc tgg ttc ttc ccc tta agc aaa acc    1872
Tyr Ser Ala Thr His Asn Gln Thr Trp Phe Phe Pro Leu Ser Lys Thr
    610                 615                 620 ttc acg ctg atg ctc ggc ggc gaa gtc ggc att gcg ggc ggc tac ggc    1920
Phe Thr Leu Met Leu Gly Gly Glu Val Gly Ile Ala Gly Gly Tyr Gly
```

```
                     625                 630                 635                 640
aga  acc  aaa  gaa  atc  ccc  ttc  ttt  gaa  aac  ttc  tac  ggc  ggc  ggc  ctg      1968
Arg  Thr  Lys  Glu  Ile  Pro  Phe  Phe  Glu  Asn  Phe  Tyr  Gly  Gly  Gly  Leu
                          645                 650                 655 ggt  tcg  gtg  cgc  gga  tac  gaa  agc  ggc  acg  ctc  ggt  ccg  aaa  gtg  tat      2016
Gly  Ser  Val  Arg  Gly  Tyr  Glu  Ser  Gly  Thr  Leu  Gly  Pro  Lys  Val  Tyr
               660                 665                 670 gac  gaa  tac  ggc  gaa  aaa  atc  agc  tac  ggc  ggc  aac  aaa  aaa  gcc  aac      2064
Asp  Glu  Tyr  Gly  Glu  Lys  Ile  Ser  Tyr  Gly  Gly  Asn  Lys  Lys  Ala  Asn
          675                 680                 685 gtc  tcc  gcc  gag  ctg  ctc  ttc  ccg  atg  cct  ggc  gcg  aaa  gac  gcg  cgc      2112
Val  Ser  Ala  Glu  Leu  Leu  Phe  Pro  Met  Pro  Gly  Ala  Lys  Asp  Ala  Arg
     690                 695                 700 acc  gtc  cgc  ctg  agc  ctg  ttt  gcc  gac  gca  ggc  agc  gtg  tgg  gac  ggc      2160
Thr  Val  Arg  Leu  Ser  Leu  Phe  Ala  Asp  Ala  Gly  Ser  Val  Trp  Asp  Gly
705                 710                 715                 720 aaa  acc  tac  gac  gac  aac  agc  agt  tcc  gcg  acc  ggc  ggc  agg  gtt  caa      2208
Lys  Thr  Tyr  Asp  Asp  Asn  Ser  Ser  Ser  Ala  Thr  Gly  Gly  Arg  Val  Gln
                         725                 730                 735 aac  att  tac  ggc  gcc  ggc  aat  acc  cat  aaa  tcc  acc  ttt  acc  aac  gaa      2256
Asn  Ile  Tyr  Gly  Ala  Gly  Asn  Thr  His  Lys  Ser  Thr  Phe  Thr  Asn  Glu
               740                 745                 750 ttg  cgc  tat  tcc  gcc  ggc  ggc  gcg  gtt  acc  tgg  ctc  tcg  cct  tta  ggc      2304
Leu  Arg  Tyr  Ser  Ala  Gly  Gly  Ala  Val  Thr  Trp  Leu  Ser  Pro  Leu  Gly
          755                 760                 765 ccg  atg  aaa  ttc  agg  tac  gcc  tac  ccg  ctg  aag  aaa  aaa  ccg  gaa  gac      2352
Pro  Met  Lys  Phe  Arg  Tyr  Ala  Tyr  Pro  Leu  Lys  Lys  Lys  Pro  Glu  Asp
     770                 775                 780 gaa  atc  caa  cgc  ttc  caa  ttc  caa  ctc  ggc  acg  acg  ttc  taa               2394
Glu  Ile  Gln  Arg  Phe  Gln  Phe  Gln  Leu  Gly  Thr  Thr  Phe
785                 790                 795

<210> SEQ ID NO 4
<211> LENGTH: 797
<212> TYPE: PRT
<213> ORGANISM: Neisseria meningitidis

<400> SEQUENCE: 4

Met  Lys  Leu  Lys  Gln  Ile  Ala  Ser  Ala  Leu  Met  Met  Leu  Gly  Ile  Ser
1                   5                   10                  15

Pro  Leu  Ala  Phe  Ala  Asp  Phe  Thr  Ile  Gln  Asp  Ile  Arg  Val  Glu  Gly
                20                  25                  30

Leu  Gln  Arg  Thr  Glu  Pro  Ser  Thr  Val  Phe  Asn  Tyr  Leu  Pro  Val  Lys
          35                  40                  45

Val  Gly  Asp  Thr  Tyr  Asn  Asp  Thr  His  Gly  Ser  Ala  Ile  Ile  Lys  Ser
     50                  55                  60

Leu  Tyr  Ala  Thr  Gly  Phe  Phe  Asp  Asp  Val  Arg  Val  Glu  Thr  Ala  Asp
65                  70                  75                  80

Gly  Gln  Leu  Leu  Leu  Thr  Val  Ile  Glu  Arg  Pro  Thr  Ile  Gly  Ser  Leu
                85                  90                  95

Asn  Ile  Thr  Gly  Ala  Lys  Met  Leu  Gln  Asn  Asp  Ala  Ile  Lys  Lys  Asn
          100                 105                 110

Leu  Glu  Ser  Phe  Gly  Leu  Ala  Gln  Ser  Gln  Tyr  Phe  Asn  Gln  Ala  Thr
     115                 120                 125

Leu  Asn  Gln  Ala  Val  Ala  Gly  Leu  Lys  Glu  Glu  Tyr  Leu  Gly  Arg  Gly
130                 135                 140

Lys  Leu  Asn  Ile  Gln  Ile  Thr  Pro  Lys  Val  Thr  Lys  Leu  Ala  Arg  Asn
145                 150                 155                 160
```

```
Arg Val Asp Ile Asp Ile Thr Ile Asp Glu Gly Lys Ser Ala Lys Ile
                165                 170                 175
Thr Asp Ile Glu Phe Glu Gly Asn Gln Val Tyr Ser Asp Arg Lys Leu
            180                 185                 190
Met Arg Gln Met Ser Leu Thr Glu Gly Gly Ile Trp Thr Trp Leu Thr
        195                 200                 205
Arg Ser Asn Gln Phe Asn Glu Gln Lys Phe Ala Gln Asp Met Glu Lys
    210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Lys Gln Thr Ile Lys
                245                 250                 255
Ile Thr Val His Glu Gly Gly Arg Phe Arg Trp Gly Lys Val Ser Ile
            260                 265                 270
Glu Gly Asp Thr Asn Glu Val Pro Lys Ala Glu Leu Glu Lys Leu Leu
        275                 280                 285
Thr Met Lys Pro Gly Lys Trp Tyr Glu Arg Gln Gln Met Thr Ala Val
    290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Glu Thr Lys Thr Val Asp
                325                 330                 335
Phe Val Leu His Ile Glu Pro Gly Arg Lys Ile Tyr Val Asn Glu Ile
            340                 345                 350
His Ile Thr Gly Asn Asn Lys Thr Arg Asp Glu Val Val Arg Arg Glu
        355                 360                 365
Leu Arg Gln Met Glu Ser Ala Pro Tyr Asp Thr Ser Lys Leu Gln Arg
    370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
        435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Thr Ala Gly
            500                 505                 510
Ala Gly Ile Arg Met Ser Val Pro Val Thr Glu Tyr Asp Arg Val Asn
        515                 520                 525
Phe Gly Leu Val Ala Glu His Leu Thr Val Asn Thr Tyr Asn Lys Ala
    530                 535                 540
Pro Lys His Tyr Ala Asp Phe Ile Lys Lys Tyr Gly Lys Thr Asp Gly
545                 550                 555                 560
Thr Asp Gly Ser Phe Lys Gly Trp Leu Tyr Lys Gly Thr Val Gly Trp
                565                 570                 575
```

-continued

```
Gly Arg Asn Lys Thr Asp Ser Ala Leu Trp Pro Thr Arg Gly Tyr Leu
                580                 585                 590

Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
        610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
                660                 665                 670

Asp Glu Tyr Gly Glu Lys Ile Ser Tyr Gly Gly Asn Lys Lys Ala Asn
            675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
                755                 760                 765

Pro Met Lys Phe Arg Tyr Ala Tyr Pro Leu Lys Lys Lys Pro Glu Asp
        770                 775                 780

Glu Ile Gln Arg Phe Gln Phe Gln Leu Gly Thr Thr Phe
785                 790                 795
```

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
cggaattcat gaaactgaaa cag                                    23

<210> SEQ ID NO 6
<211> LENGTH: 18
<212> TYPE: DNA
<213> ORGANISM: Artificial Sequence
<220> FEATURE:
<223> OTHER INFORMATION: PCR primer

<400> SEQUENCE: 6
ttgcagtttt tgcaattc                                          18

<210> SEQ ID NO 7
<211> LENGTH: 59
<212> TYPE: DNA
<213> ORGANISM: Neisseria gonorrhoeae

<400> SEQUENCE: 7
tagattttac gtttcggaat gcagtctgaa accgcattcc gcaccacaag gaacttacg    59

<210> SEQ ID NO 8
<211> LENGTH: 67

```
<212> TYPE: DNA
<213> ORGANISM: Neisseria gonorrhoeae

<400> SEQUENCE: 8
cccgcaaatg ccgtctgaag cccttgagac ggcatttcgc ggcaacatcc gaaggagttt    60
taccatg                                                              67
```